United States Patent [19]

Taniguchi et al.

[11] Patent Number: 5,026,850
[45] Date of Patent: Jun. 25, 1991

[54] PYRIDAZINONE DERIVATIVES, PREPARATION THEREOF, AND INSECTICIDAL, ACARICIDAL, FUNGICIDAL COMPOSITIONS

[75] Inventors: Masakazu Taniguchi, Funabashi; Masatoshi Baba, Narashino; Yoshinori Ochiai, Hasuda; Masayoshi Hirose, Kawaguchi; Kiminori Hirata, Urawa, all of Japan

[73] Assignee: Nissan Chemical Industries, Ltd., Tokyo, Japan

[21] Appl. No.: 362,348

[22] Filed: Jun. 6, 1989

Related U.S. Application Data

[60] Division of Ser. No. 27,191, Mar. 17, 1987, Pat. No. 4,877,787, which is a continuation of Ser. No. 621,458, Jun. 18, 1984, abandoned.

[30] Foreign Application Priority Data

Jun. 23, 1983 [JP] Japan .................. 58-113409
Jul. 29, 1983 [JP] Japan .................. 58-138878

[51] Int. Cl.$^5$ .................. C07D 237/18; A61K 31/50; A01N 43/58
[52] U.S. Cl. .................. 544/240
[58] Field of Search .................. 514/240

[56] References Cited

U.S. PATENT DOCUMENTS

| 2,832,780 | 4/1958 | King | 544/239 |
| 3,137,696 | 6/1964 | Neicheneder | 544/240 |
| 3,346,577 | 10/1967 | Nakagome | 544/240 |
| 4,177,273 | 12/1979 | Bennett | 544/240 |
| 4,571,397 | 2/1986 | Taniguchi | 544/239 |
| 4,576,630 | 3/1986 | Parg et al. | 544/240 |
| 4,663,324 | 5/1987 | Graf et al. | 544/240 |
| 4,783,462 | 11/1988 | Mutsukado et al. | 514/249 |
| 4,837,217 | 6/1989 | Ogura et al. | 544/239 |
| 4,874,861 | 10/1989 | Ogura et al. | 544/239 |

FOREIGN PATENT DOCUMENTS

| 78450 | 5/1983 | European Pat. Off. . |
| 88384 | 9/1983 | European Pat. Off. . |
| 134439 | 3/1985 | European Pat. Off. . |
| 135076 | 3/1985 | European Pat. Off. . |
| 183212 | 6/1986 | European Pat. Off. . |
| 193853 | 9/1986 | European Pat. Off. . |
| 199281 | 10/1986 | European Pat. Off. . |
| 1445475 | 11/1968 | Fed. Rep. of Germany . |
| 3143303 | 5/1983 | Fed. Rep. of Germany . |
| 3328770 | 2/1985 | Fed. Rep. of Germany . |
| 41-2459 | 2/1966 | Japan . |
| 41-2788 | 2/1966 | Japan . |
| 42-1302 | 1/1967 | Japan . |
| 42-9344 | 5/1967 | Japan . |
| 43-11902 | 5/1968 | Japan . |
| 43-11903 | 5/1968 | Japan . |
| 43-11904 | 5/1968 | Japan . |
| 43-11905 | 5/1968 | Japan . |
| 43-11906 | 5/1968 | Japan . |
| 43-11907 | 5/1968 | Japan . |
| 43-11908 | 5/1968 | Japan . |
| 43-11909 | 5/1968 | Japan . |
| 44-8857 | 4/1969 | Japan . |
| 44-8858 | 4/1969 | Japan . |
| 44-8859 | 4/1969 | Japan . |
| 44-8860 | 4/1969 | Japan . |
| 44-8861 | 4/1969 | Japan . |
| 44-124216 | 6/1969 | Japan . |

OTHER PUBLICATIONS

Kaju, Chemical Abstracts 70, 28883; (1969).
Gymer, Chemical Abstract No. 114552g, vol. 93, 1980.
Wilson, Chemical Abstract No. 20533h, vol. 91, 1979.
Chemical Abstract No. 106728h, vol. 69, 1968.
Taniguchi et al., Chem. Abs 100, 34565 (9-14-83).
Kaji I, Chem. Abs. 71, 30484u (1969).
Beska et al., Chem Abs 78, 124,615j (1972).
Kaji II, Chem Abs 69, 106726F (1968).
Japanese Patent Abstract of Laid-Open Appln JP 60-4173, May 16, 1985, vol. 9, No. 112 (c-281) (1835).
Japanese Patent Abstract of Laid-Open Appln JP 60-54319, Jul. 30, 1985, vol. 9, No. 184 (c-294) (1907).

Primary Examiner—Mark L. Berch
Attorney, Agent, or Firm—Oliff & Berridge

[57] ABSTRACT

Compounds of the formula:

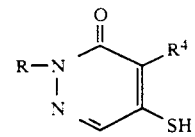

wherein R is a member selected from the group consisting of lower alkyls having from 2 to 4 carbon atoms; and chlorine and bromine. The compounds are useful as active ingredients in, e.g., insecticidal, acaricidal, nematicidal, fungicidal and expellant compositions.

3 Claims, No Drawings

PYRIDAZINONE DERIVATIVES, PREPARATION THEREOF, AND INSECTICIDAL, ACARICIDAL, FUNGICIDAL COMPOSITIONS

This is a Division of application Ser. No. 027,191 filed Mar. 17, 1987, now U.S. Pat. No. 4,877,787 which in turn is a continuation of application Ser. No. 621,458, filed June 18, 1984 (now abandoned).

BACKGROUND OF THE INVENTION (1) Field of the Invention

This invention relates to novel 3(2H)-pyridazinone derivatives; preparation thereof; insecticidal, acarical, nematicidal, fungicidal compositions for agricultural and horticultural uses; and expellent compositions for ticks parasitic on animals; said compositions containing said derivatives as an active ingredient.

(2) Description of the Prior Art

Hitherto, there have been reported various 3(2H)-pyridazinone derivatives which have thioether bonding as in the compounds of the present invention. Among them, there have been known the compounds listed in Table 1 below and the physiological activities thereof.

The physiological activities of all the compounds listed in Table 1 are restricted to fungicidal, central nerve depressing- and/or herbicidal actions. It has not been reported at all that these compounds exhibit excellent insecticidal, acaricidal, nematicidal activities which are found in the compounds of the present invention. The compounds according to the present invention have excellent insecticidal, acaricidal and nematicidal activities in addition to fungicidal action. These activities are attributed to the specific structures of the compounds of the present invention. Namely, the compounds of the invention are unique in that they have a straight or branched $C_2$ to $C_6$ alkyl group on the 2-position of the pyridazinone ring and also a substituted benzylthio group on the 5-position of said ring. The prior art literature has disclosed neither the compounds of the invention specifically nor physiological activities such as insecticidal, acaricidal, nematicidal activities of the compounds.

TABLE 1

| Compound | Physiological activity | Japanese Patent Publication No. (Publication Date) |
|---|---|---|
| 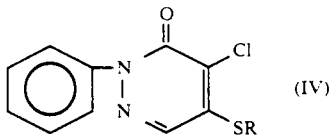<br>R: alkyl, benzyl or 4-chlorobenzyl (IV) | fungicidal action<br>central nerve-depressing action | 09344/67 (5/11/67)<br>08860/69 (4/24/69) |
| 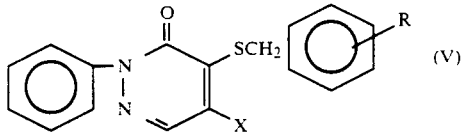<br>R: Hydrogen or a halogen<br>X: a halogen or thiol (V) | pressor action | 11902/68 (5/20/68)<br>11903/68 (5/20/68)<br>11904/68 (5/20/68)<br>08857/69 (4/24/69)<br>08859/69 (4/24/69)<br>12421/69 (6/5/69) |
| 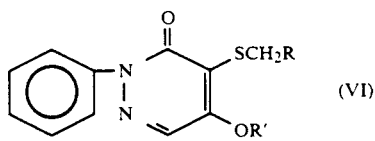<br>R: phenyl furyl or thienyl<br>$R^1$: a lower alkyl (VI) | pressor action<br>central nerve-depressing action<br>antifungal action | 11905/68 (5/20/68)<br>11908/68 (5/20/68) |
| 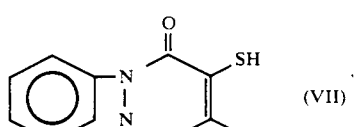<br>R: a halogen or a lower alkylthio (VII) | antifungal action | 08860/69 (4/24/69)<br>08861/69 (4/24/69) |

TABLE 1-continued

| Compound | Physiological activity | Japanese Patent Publication No. (Publication Date) |
|---|---|---|
| (VIII) R: phenyl, chlorine-substituted phenyl, pyridyl, furyl or thienyl | pressor action antifungal action anti-acetyl choline action | 01302/67 (1/23/67) 11904/68 (5/20/68) 11906/68 (5/20/68) 11907/68 (5/20/68) 11909/68 (5/20/68) 08858/69 (4/24/68) |
| (IX) X: O or S | antifungal action | 02459/66 (2/17/66) 02788/66 (2/21/66) |
| (X) R: hydrogen, methyl, ethyl or benzyl | fungicidal action | Chemical Abstracts 93, 114552g |
| (XI) | fungicidal action | Chemical Abstracts 91, 20533h and 74637p |
| (XII) R: hydrogen, an alkyl, phenyl or a halophenyl | | |
| (XIII) R: hydrogen or phenyl $R^2$: an alkyl, phenyl, or $-CH_2COOH$ | herbicidal action | Japanese Patent Publication No. No. 03798/65 |

All the compounds represented by the general formulae IV through VIII are apparently different from those of the present invention of the formula I given below in that the former compounds have phenyl group at 2-position. On the other hand, the compounds of the general formula IX are also apparently different therefrom in that the 2-position of the former is not substituted. Moreover, the thiol compounds and the salts thereof having the formula X are reported to have fungicidal activity and are different from those of the present invention in that the former have a substituted benzylthio group at 5-position.

The present inventors have conducted intensive research on the preparation of the novel compounds of the formula I given below as well as on activities thereof as an agricultural drug, and have found that the compounds of the formula I are useful for the control of agricultural and horticultural insect pests and acari, for the prevention of blight and for expelling ticks parasitic on animals to accomplish the invention.

SUMMARY OF THE INVENTION

An object of this invention is to provide novel 3(2H)pyridazinone derivatives which have insecticidal, acaricidal bactericidal and nematicidal activities.

Another object of this invention is to provide a process for preparing such 3(2H)-pyridazinone derivatives.

Further object of this invention is to provide bactericidal, insecticidal, acaricidal, nematicidal compositions containing a 3(2H)-pyridazinone derivative as an active ingredient.

Other objects of this invention will become apparent from the description given below.

The 3(2H)-pyridazinone derivatives according to the invention have the general formula (I):

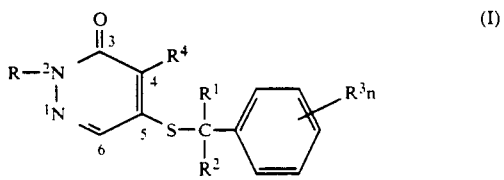

wherein, R denotes a straight or branched $C_2$ to $C_6$ alkyl, $R^1$ and $R^2$ denote each independently hydrogen or a lower alkyl, $R^4$ denotes a halogen, $R^3$ denotes a halogen; a straight or branched $C_1$ to $C_{12}$ alkyl, a cycloalkyl unsubstituted or substituted by a lower alkyl; a straight or branched $C_1$ to $C_{12}$ alkoxy; a lower haloalkyl; a lower haloalkoxy; —CN; —NO$_2$;

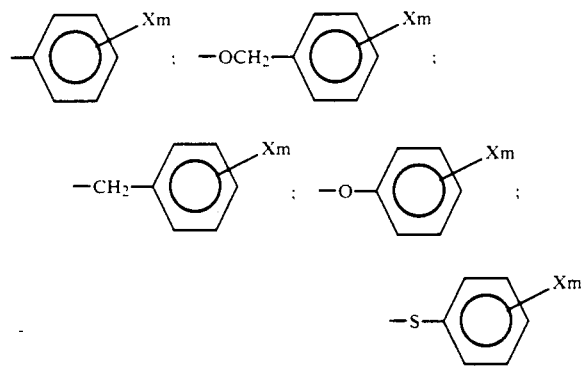

(wherein X denotes a halogen, a lower alkyl, a cycloalkyl, a lower alkoxy, a lower haloalkyl, a lower haloalkoxy, —CN or —NO$_2$ and m denotes 0 or an integer of 1 to 5, said X being the same or different when m is an integer of 2 to 5); a pyridyloxy may be substituted by a halogen and/or —CF$_3$; a quinoxalyloxy which may be substituted by a halogen and/or —CF$_3$; a lower alkenyloxy; a lower alkylthio; a lower haloalkylthio; —Si(CH$_3$)$_3$; —OH; —N(CH$_3$)$_2$; —SCN; —COOCH$_3$; or —OCH(CH$_3$)COOC$_2$H$_5$, and n denotes an integer of 1 to 5, said $R^3$ being the same or different when n is an integer of 2 to 5.

The present invention also comprises a process for preparation of said derivatives; insecticidal, acaricidal, nematicidal, and/or fungicidal compositions for agricultural and horticultural uses; and compositions for expelling ticks that are parasitic on animals; said compositions containing said derivatives as an active ingredient.

The compounds according to the present invention particularly have high insecticidal and acaricidal activities and exhibit excellent immediate effects and residual activity.

DESCRIPTION OF THE PREFERRED EMBODIMENTS

The "lower alkyl" including the lower alkyl moieties contained in the groups such as "lower alkoxy", "lower haloalkyl", "lower haloalkoxy", "lower alkylthio" and "lower haloalkylthio" are usually a straight or branched alkyl of 1 to 6 carbon atoms, preferably of 1 to 4 carbon atoms such as methyl, ethyl, n-propyl, i-propyl, n-butyl, iso-butyl, sec.-butyl or tert.-butyl.

The "lower alkenyl" contained in the lower alkenyloxy is usually a straight or branched alkenyl of 2 to 6 carbon atoms, preferably of 2 to 4 carbon atoms such as ethenyl, n-propenyl, n-propadienyl, i-propenyl, n-butenyl, n-butadienyl, n-butatrienyl, sec.-butenyl, and sec.-butadienyl.

The term "halogen" and halogens contained in the groups such as "haloalkyl", "haloalkoxy" and "haloalkylthio" mean florine, chlorine, bromine, iodine atom or a mixture thereof.

The "cycloalkyl" as $R^3$ or as a substituent X preferably has 3 to 6 carbon atoms.

R is preferably a straight or branched alkyl of 2 to 4 carbon atoms, such as ethyl, n-propyl, i-propyl, n-butyl, iso-butyl, sec.-butyl, or tert.-butyl, and most preferably tert.-butyl.

$R^1$ and $R^2$ are each preferably hydrogen or a straight or branched lower alkyl of 1 to 3 carbon atoms such as methyl, ethyl, n-propyl or i-propyl, and more preferably hydrogen, methyl or ethyl.

$R^3$ is preferably a straight or branched alkyl of $C_3$ to $C_8$, (such as i-propyl, t-butyl, i-butyl, n-hexyl, n-heptyl, n-octyl), $C_2$ to $C_8$ alkoxyl (such as ethoxy, n-propoxy, i-propoxy, n-pentyloxy, n-hexyloxy, n-heptyloxy). Further $R^3$ is preferably phenyl,

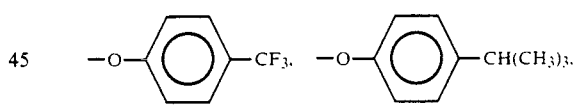

—OCHF$_2$, cyclopropyl, cyclohexyl, allyloxy, 2-butenyloxy and —Si(CH$_3$)$_3$. Most preferably $R^3$ is t-butyl, phenyl, cyclohexyl and

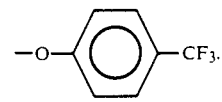

The preferable position of $R^3$ is 4-position.

$R^4$ is preferably chlorine or bromine, more preferably chlorine.

n is preferably an integer of 1 to 5, more preferably 1 or 2, and most preferably 1.

The following compounds are most important from the viewpoint of pesticidal activities:

| Compound No. | |
|---|---|
| 70. | 2-tert.butyl-4-chloro-5-(4-tert.-butyl-α-methyl- |

| Compound No. | |
|---|---|
| | benzylthio)-3(2H)-pyridazinone |

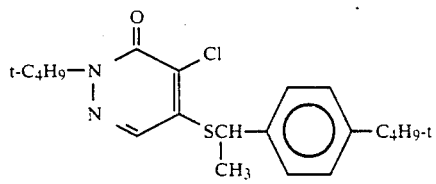

| 81. | 2-tert.-butyl-4-chloro-5-(4-tert.-butyl-benzylthio-3(2H)-pyridazinone |
|---|---|

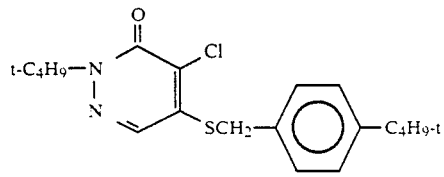

| 88. | 2-tert.-butyl-4-chloro-5-(4-cyclohexyl-benzylthio)-3(2H)-pyridazinone |
|---|---|

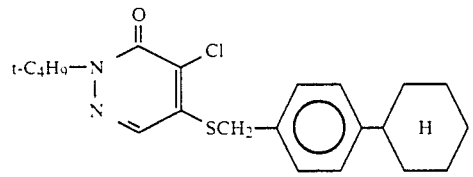

| 95. | 2-tert.-butyl-4-chloro-5-(4-phenyl-benzyl-thio)-3(2H)-pyridazinone |
|---|---|

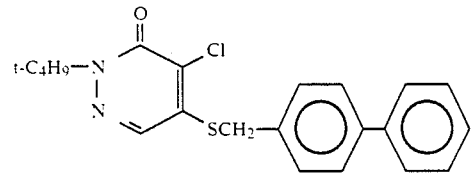

| 103. | 2-tert.butyl-4-chloro-5-(4-iso-propyl-α-methylbenzylthio)-3(2H)-pyridazinone |
|---|---|

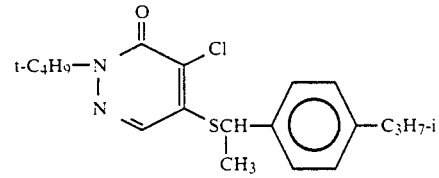

| 106. | 2-tert.-butyl-4-chloro-5-(4-cyclohexyl-α-methylbenzylthio)-3(2H)-pyridazinone |
|---|---|

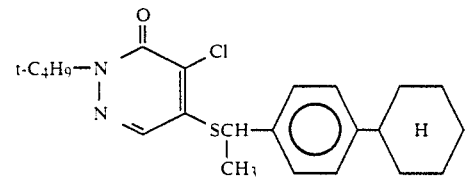

| 109. | 2-tert.-butyl-4-chloro-5-(4-phenyl-α-methyl-benzylthio)-3(2H)-pyridazinone |
|---|---|

-continued

| Compound No. | |
|---|---|
| | 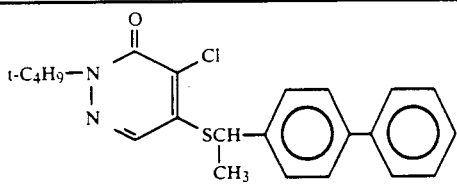 |
| 129. | 2-tert.-butyl-4-chloro-5-(4-allyloxy-benzylthio)-3(2H)-pyridazinone |
| | 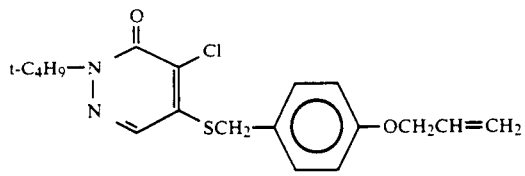 |
| 133. | 2-tert.-butyl-4-chloro-5-(4-trimethylsilyl-benzylthio)-3(2H)-pyridazinone |
| | 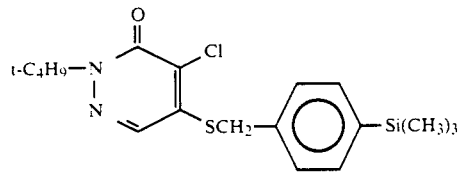 |
| 138. | 2-tert.-butyl-4-chloro-5-(4-difluoromethoxy-benzylthio)-3(2H)-pyridazinone |
| | 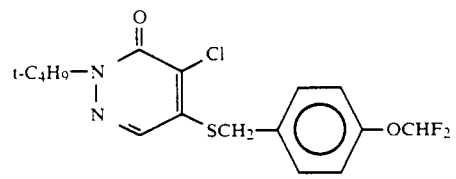 |
| 141. | 2-tert.-butyl-4-chloro-5-(4-cyclopropyl-benzylthio)-3(2H)-pyridazinone |
| | 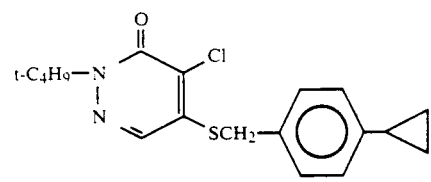 |
| 153. | 2-tert.-butyl-4-chloro-5-(4-ethoxy-benzylthio)-3(2H)-pyridazinone |
| | 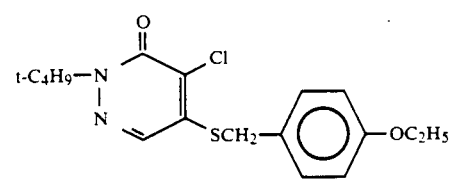 |
| 154. | 2-tert.-butyl-4-chloro-5-(4-n-propoxy-benzylthio)-3(2H)-pyridazinone |
| | 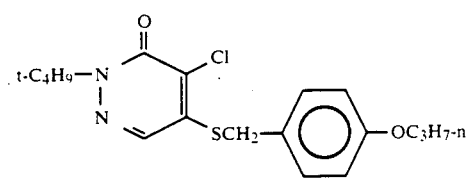 |

-continued

| Compound No. | |
|---|---|
| 155. | 2-tert.-butyl-4-chloro-5-(4-iso-butyl-benzythio)-3(2H)-pyridazinone |

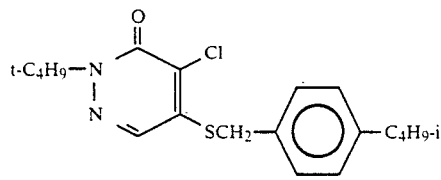

| | |
|---|---|
| 157. | 2-tert.-butyl-4-chloro-5-(4-n-hexyl-benzylthio)-3(2H)-pyridazinone |

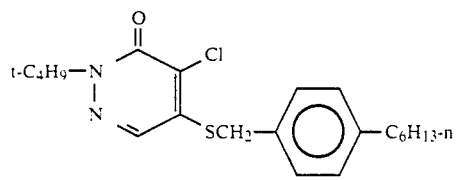

| | |
|---|---|
| 158. | 2-tert.-butyl-4-chloro-5-(4-n-heptyl-benzylthio)-3(2H)-pyridazinone |

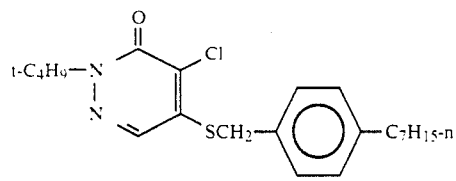

| | |
|---|---|
| 159. | 2-tert.-butyl-4-chloro-5-(4-n-octyl-benzylthio)-3(2H)-pyridazinone |

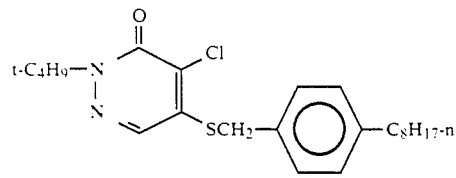

| | |
|---|---|
| 163. | 2-tert.-butyl-4-chloro-5-(4-iso-propoxy-benzylthio)-3(2H)-pyridazinone |

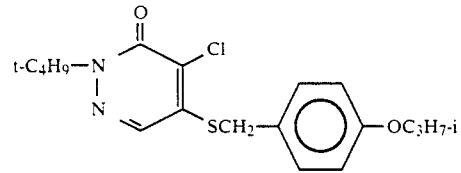

| | |
|---|---|
| 169. | 2-tert.-butyl-4-chloro-5-(4-n-pentyloxy-benzylthio)-3(2H)-pyridazinone |

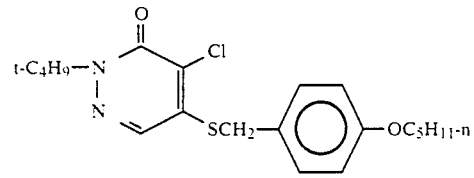

| | |
|---|---|
| 170. | 2-tert.-butyl-4-chloro-5-(4-n-hexyloxy-benzylthio)-3(2H)-pyridazinone |

| Compound No. | |
|---|---|
| -continued | |

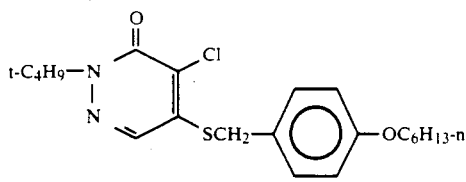

| 171. | 2-tert.-butyl-4-chloro-5-(4-n-heptyloxy-benzylthio)-3(2H)-pyridazinone |

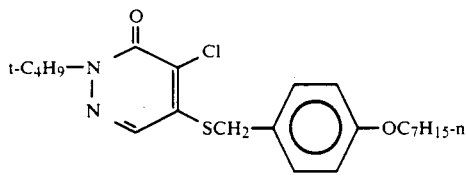

| 180. | 2-tert.-butyl-4-chloro-5-[4-(2-butenyloxy)-benzylthio]-3(2H)-pyridazinone |

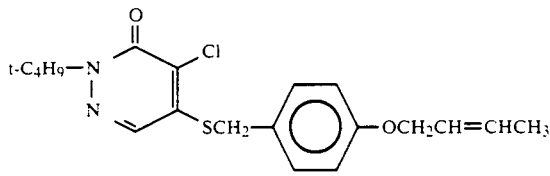

| 243. | 2-tert.-butyl-4-chloro-5-[4-(4-trifluoromethyl-phenoxy)-benzylthio]-3(2H)-pyridazinone |

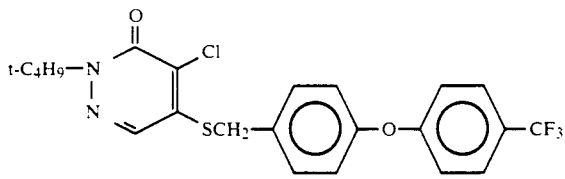

| 245. | 2-tert.-butyl-4-chloro-5-[4-(4-tert.-butyl-phenoxy)-α-methylbenzylthio]-3(2H)-pyridazinone |

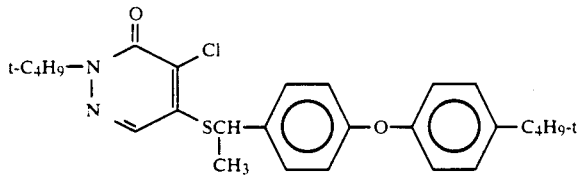

More preferable compounds are those of Compound Nos. 70, 81, 88, 95, 106, 109 and 243.

The compounds listed in Table 2 below are exemplified as the compounds to be included in the present invention. However, it should be understood that the compounds in Table 2 are only illustrative and not to restrict the invention. Incidentally, a compound of the invention containing asymmetric carbon atom(s) includes optically active (+) compound and (−) compound.

TABLE 2

Compounds of the formula I:

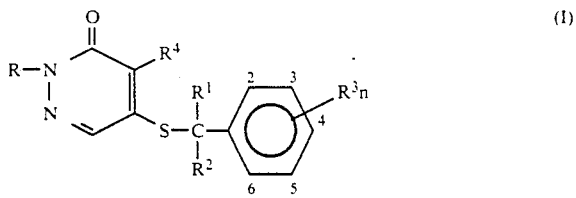

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 1 | Et | H | H | Cl | 4-t-Bu |
| 2 | Et | H | H | Cl | 4-F |
| 3 | Et | H | H | Cl | 3-$CF_3$ |
| 4 | Et | H | H | Cl | 4-phenyl |
| 5 | Et | H | H | Cl | 4-$OCH_2$-phenyl |
| 6 | Et | H | H | Cl | 4-cyclohexyl |
| 7 | Et | Me | H | Cl | 4-$OCF_2CF_3$ |
| 8 | Et | Me | Me | Cl | 4-t-Bu |
| 9 | Et | H | H | Br | 4-cyclohexyl |
| 10 | Et | H | H | Br | 4-$CF_3$ |
| 11 | Et | H | H | Br | 2,3,4,5,6-$F_5$ |
| 12 | Et | Me | H | Br | 4-t-Bu |
| 13 | Et | Me | H | Br | 4-F |
| 14 | n-Pr | H | H | Cl | 4-t-Bu |
| 15 | n-Pr | H | H | Cl | 4-cyclohexyl |
| 16 | n-Pr | H | H | Cl | 4-phenyl |
| 17 | n-Pr | H | H | Cl | 4-F |
| 18 | n-Pr | H | H | Cl | 2,4-$Cl_2$ |
| 19 | n-Pr | Me | H | Cl | 4-t-Bu |
| 20 | n-Pr | Me | H | Cl | 4-$OCH_2$-phenyl-$CF_3$ |
| 21 | n-Pr | Me | H | Cl | 2,4-$Cl_2$ |
| 22 | n-Pr | H | H | Cl | 3,5-$Cl_2$ |
| 23 | n-Pr | H | H | Cl | 3-CN |
| 24 | n-Pr | Me | H | Cl | 4-i-Pr |
| 25 | n-Pr | Me | H | Cl | 4-Cl |
| 26 | n-Pr | Me | Me | Cl | 4-t-Bu |
| 27 | n-Pr | H | H | Br | 2-$OCF_3$ |

TABLE 2-continued

Compounds of the formula I:

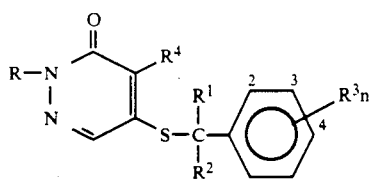

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3$n |
|---|---|---|---|---|---|
| 28 | n-Pr | H | H | Br | 4-OCH$_2$–(phenyl with 2-Cl, 4-Cl) |
| 29 | i-Pr | H | H | Cl | 3,4-Cl$_2$ |
| 30 | i-Pr | H | H | Cl | 4-t-Bu |
| 31 | i-Pr | H | H | Cl | 2-NO$_2$ |
| 32 | i-Pr | H | H | Cl | 4-OEt |
| 33 | i-Pr | Et | Me | Cl | 3-Br |
| 34 | i-Pr | n-Pr | H | Cl | 4-Me |
| 35 | i-Pr | H | H | Br | 2-OMe |
| 36 | i-Pr | H | H | Br | 3-CF$_3$ |
| 37 | i-Pr | Me | H | Br | 4-F |
| 38 | i-Pr | Me | Me | Br | 4-OCH$_2$–(phenyl with 4-CF$_3$) |
| 39 | n-Bu | H | H | Cl | 4-Br |
| 40 | n-Bu | H | H | Cl | 3,4-Cl$_2$ |
| 41 | n-Bu | H | H | Cl | 2-CF$_3$ |
| 42 | n-Bu | H | H | Cl | 3-OCH$_2$CF$_3$ |
| 43 | n-Bu | Me | H | Cl | 4-(phenyl) |
| 44 | n-Bu | n-Bu | H | Cl | 4-(phenyl) |
| 45 | n-Bu | Et | Et | Cl | 4-(phenyl) |
| 46 | n-Bu | H | H | Br | 3-OCF$_3$ |
| 47 | n-Bu | H | H | Br | 4-OCH$_2$–(phenyl with 4-CF$_3$) |
| 48 | n-Bu | H | H | Br | 2,4-Cl$_2$ |
| 49 | i-Bu | H | H | Cl | 3-Me |
| 50 | i-Bu | H | H | Cl | 3,4-(Me)$_2$ |
| 51 | i-Bu | H | H | Cl | 3-(cyclopentyl-H) |
| 52 | i-Bu | H | H | Cl | 2-Cl, 4-Me |

TABLE 2-continued

Compounds of the formula I:

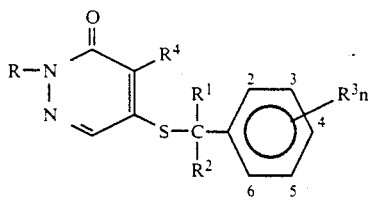

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 53 | i-Bu | Me | H | Cl | 2-Cl, 4-F |
| 54 | i-Bu | Et | H | Cl | 2,6-Cl$_2$ |
| 55 | i-Bu | Et | Me | Br | 4-Cl |
| 56 | s-Bu | H | H | Cl | 2-Cl, 4-F |
| 57 | s-Bu | H | H | Cl | 2-Me, 4-Cl |
| 58 | s-Bu | H | H | Cl | 4-(cyclohexyl) |
| 59 | s-Bu | H | H | Cl | 4-t-Bu |
| 60 | s-Bu | H | H | Cl | 2,5-(Me)$_2$ |
| 61 | s-Bu | Me | H | Cl | 4-F |
| 62 | s-Bu | Et | H | Cl | 4-F |
| 63 | s-Bu | H | H | Cl | 4-OCH$_2$-(2,6-diF-phenyl) |
| 64 | s-Bu | H | H | Br | 4-phenyl |
| 65 | s-Bu | H | H | Br | 4-CN |
| 66 | s-Bu | H | H | Br | 3-CF$_3$ |
| 67 | s-Bu | H | H | Br | 2-F, 4-CF$_3$ |
| 68 | s-Bu | Me | H | Br | 2-F, 4-Cl |
| 69 | s-Bu | i-Pr | H | Br | 4-OCF$_3$ |
| 70 | t-Bu | Me | H | Cl | 4-t-Bu |
| 71 | optically active compound (+) of Compound No. 70 |
| 72 | optically active compound (−) of Compound No. 70 |
| 73 | t-Bu | H | H | Cl | 4-O-(6-chloroquinoxalin-2-yl) |
| 74 | t-Bu | H | H | Cl | 4-O-(6-trifluoromethylquinoxalin-2-yl) |
| 75 | t-Bu | H | H | Cl | 4-O-(5-trifluoromethylpyridin-2-yl) |
| 76 | t-Bu | H | H | Cl | 4-O-(quinoxalin-2-yl) |

TABLE 2-continued

Compounds of the formula I:

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 77 | t-Bu | H | H | Cl | 2-Me |
| 78 | t-Bu | H | H | Cl | 3-Me |
| 79 | t-Bu | H | H | Cl | 4-Me |
| 80 | t-Bu | H | H | Cl | 4-i-Pr |
| 81 | t-Bu | H | H | Cl | 4-t-Bu |
| 82 | t-Bu | H | H | Cl | 2-Cl |
| 83 | t-Bu | H | H | Cl | 2,4-$Cl_2$ |
| 84 | t-Bu | H | H | Cl | 3,4-$Cl_2$ |
| 85 | t-Bu | H | H | Cl | 2-Cl, 4-Me |
| 86 | t-Bu | H | H | Cl | 2-F, 4-Cl |
| 87 | t-Bu | H | H | Cl | 4-F |
| 88 | t-Bu | H | H | Cl | 4-(cyclohexyl) |
| 89 | t-Bu | H | H | Cl | 4-(2-methylcyclohexyl) |
| 90 | t-Bu | H | H | Cl | 3-$CF_3$ |
| 91 | t-Bu | H | H | Cl | 3-OMe |
| 92 | t-Bu | H | H | Cl | 4-$OCF_3$ |
| 93 | t-Bu | H | H | Cl | 2-$OCF_3$, 4-Cl |
| 94 | t-Bu | H | H | Cl | 2,3,4,5,6-$F_5$ |
| 95 | t-Bu | H | H | Cl | 4-phenyl |
| 96 | t-Bu | H | H | Cl | 4-(4-chlorophenyl) |
| 97 | t-Bu | H | H | Cl | 4-Br |
| 98 | t-Bu | H | H | Cl | 2-$OCH_2$-phenyl |
| 99 | t-Bu | H | H | Cl | 4-$OCH_2$-phenyl |
| 100 | t-Bu | H | H | Cl | 4-$OCH_2$-(4-$CF_3$-phenyl) |
| 101 | t-Bu | Me | H | Cl | 3-Me |
| 102 | t-Bu | Me | H | Cl | 4-Me |
| 103 | t-Bu | Me | H | Cl | 4-i-Pr |

TABLE 2-continued

Compounds of the formula I:

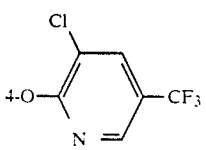

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3{}_n$ |
|---|---|---|---|---|---|
| 104 | t-Bu | H | H | Cl |  |
| 105 | t-Bu | Me | H | Cl | 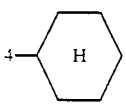 |
| 106 | t-Bu | Me | H | Cl | 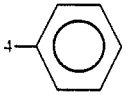 |
| 107 | t-Bu | Me | H | Cl | 4-Br |
| 108 | t-Bu | Me | H | Cl | 4-Cl |
| 109 | t-Bu | Me | H | Cl | 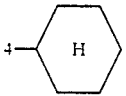 |
| 110 | t-Bu | Et | H | Cl | 4-t-Bu |
| 111 | t-Bu | Me | Me | Cl | 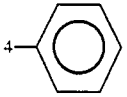 |
| 112 | t-Bu | H | H | Cl | 2-$NO_2$ |
| 113 | t-Bu | H | H | Br | 4-Me |
| 114 | t-Bu | H | H | Br | 4-F |
| 115 | t-Bu | Et | H | Cl | 4-Cl |
| 116 | t-Bu | H | H | Br | 4-$CF_3$ |
| 117 | t-Bu | H | H | Br | 2-$OCH_2CF_3$ |
| 118 | t-Bu | H | H | Br | 4-$OCF_3$ |
| 119 | t-Bu | H | H | Br | 4-CN |
| 120 | t-Bu | H | H | Br | 3-$NO_2$ |
| 121 | t-Bu | H | H | Br | 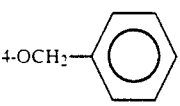 |
| 122 | t-Bu | H | H | Br | 4-$OCH_2$— |
| 123 | t-Bu | Me | H | Br | 2-F |

TABLE 2-continued

Compounds of the formula I:

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 124 | t-Bu | Me | H | Br | 4-OCH$_2$-C$_6$H$_4$-Me |
| 125 | t-Bu | n-Pr | Me | Br | 4-C$_6$H$_5$ |
| 126 | t-Bu | H | H | Cl | 4-OCH$_2$-C$_6$H$_4$-Cl |
| 127 | t-Bu | H | H | Cl | 4-OCH$_2$-C$_6$H$_4$-Me |
| 128 | t-Bu | H | H | Cl | 4-OCH$_2$-C$_6$H$_4$(2-Me) |
| 129 | t-Bu | H | H | Cl | 4-OCH$_2$CH=CH$_2$ |
| 130 | t-Bu | H | H | Cl | 4-SC$_4$H$_9$-n |
| 131 | t-Bu | H | H | Cl | 4-SMe |
| 132 | t-Bu | H | H | Cl | 3-OC$_4$H$_9$-n |
| 133 | t-Bu | H | H | Cl | 4-Si(Me)$_3$ |
| 134 | t-Bu | Me | H | Cl | 4-C$_6$H$_4$-Cl |
| 135 | t-Bu | Me | H | Cl | 4-C$_6$H$_4$-Me |
| 136 | t-Bu | H | H | Cl | 4-SCHF$_2$ |
| 137 | t-Bu | H | H | Cl | 4-OCH$_2$CH$_2$CH$_2$Cl |
| 138 | t-Bu | H | H | Cl | 4-OCHF$_2$ |
| 139 | t-Bu | H | H | Br | 4-t-Bu |
| 140 | t-Bu | H | H | Br | 4-Cl |
| 141 | t-Bu | H | H | Cl | 4-cyclopropyl(H) |
| 142 | t-Bu | H | H | Cl | 4-C(Me)$_2$CH$_2$Cl |
| 143 | t-Bu | H | H | Cl | 4-OCHC(Me)=CH$_2$ |
| 144 | t-Bu | H | H | Cl | 3,5-(t-Bu)$_2$, 4-OH |
| 145 | t-Bu | H | H | Cl | 3,5-(Br)$_2$, 4-OH |

TABLE 2-continued

Compounds of the formula I:

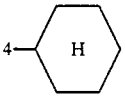

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 146 | t-Bu | H | H | Br | 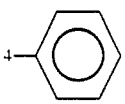 |
| 147 | t-Bu | H | H | Br | 4-n-Bu |
| 148 | t-Bu | H | H | Br | 4-$OC_6H_{13}$-n |
| 149 | t-Bu | Me | H | Br | 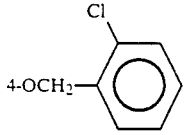 |
| 150 | t-Bu | H | H | Cl | 4-$N(Me)_2$ |
| 151 | t-Bu | H | H | Cl | 3-OMe, 4-OPr-i |
| 152 | t-Bu | H | H | Cl | 4-I |
| 153 | t-Bu | H | H | Cl | 4-OEt |
| 154 | t-Bu | H | H | Cl | 4-OPr-n |
| 155 | t-Bu | H | H | Cl | 4-i-Bu |
| 156 | t-Bu | H | H | Cl | 4-n-Bu |
| 157 | t-Bu | H | H | Cl | 4-n-$C_6H_{13}$ |
| 158 | t-Bu | H | H | Cl | 4-n-$C_7H_{15}$ |
| 159 | t-Bu | H | H | Cl | 4-n-$C_8H_{17}$ |
| 160 | t-Bu | H | H | Cl | 4-s-Bu |
| 161 | t-Bu | H | H | Cl | 4-t-$C_5H_{11}$ |
| 162 | t-Bu | H | H | Cl | 4-COOMe |
| 163 | t-Bu | H | H | Cl | 4-OPr-i |
| 164 | t-Bu | H | H | Cl | 4-$OCH_2CH(Et)Bu$-n |
| 165 | t-Bu | H | H | Cl | 4-$OC_9H_{19}$-n |
| 166 | t-Bu | H | H | Cl | 4-$OC_{11}H_{23}$-n |
| 167 | t-Bu | Me | H | Cl | 4-$OC_{10}H_{21}$-n |
| 168 | t-Bu | H | H | Cl | 4-$OC_4H_9$-n |
| 169 | t-Bu | H | H | Cl | 4-$OC_5H_{11}$-n |
| 170 | t-Bu | H | H | Cl | 4-$OC_6H_{13}$-n |
| 171 | t-Bu | H | H | Cl | 4-$OC_7H_{15}$-n |
| 172 | t-Bu | H | H | Cl | 4-$OC_8H_{17}$-n |
| 173 | t-Bu | H | H | Cl | 2,6-$(Me)_2$, 4-t-Bu |
| 174 | t-Bu | H | H | Cl | 3,5-$Br_2$, 4-OPr-i |
| 175 | t-Bu | H | H | Cl | 4-Cl |
| 176 | t-Bu | H | H | Cl | 4-$CF_3$ |
| 177 | t-Bu | H | H | Cl | 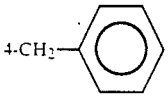 |
| 178 | t-Bu | H | H | Cl | 4-$CH_2$-⌬ |
| 179 | t-Bu | H | H | Cl | 4-OCH(Me)COOEt |
| 180 | t-Bu | H | H | Cl | 4-$OCH_2CH=CH-Me$ |
| 181 | t-Bu | H | H | Cl | 4-SCN |
| 182 | n-Pen | H | H | Cl | 4-Cl |
| 183 | n-Pen | H | H | Cl | 3-Me |

TABLE 2-continued

Compounds of the formula I:

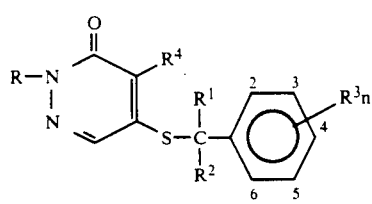

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 184 | n-Pen | H | H | Cl | 4-cyclohexyl (H) |
| 185 | n-Pen | Me | H | Cl | 4-CN |
| 186 | n-Pen | Et | H | Cl | 3-CF$_3$ |
| 187 | n-Pen | Et | Et | Cl | 4-phenyl |
| 188 | n-Pen | H | H | Br | 2-OCH$_2$—⟨phenyl⟩—OCF$_3$ |
| 189 | n-Pen | H | H | Br | 2-Cl, 4-Me |
| 190 | n-Pen | Me | H | Br | 2-Me, 4-Cl |
| 191 | i-Pen | H | H | Cl | 4-Br |
| 192 | i-Pen | H | H | Cl | 4-NO$_2$ |
| 193 | i-Pen | H | H | Cl | 4-cyclopentyl (H) |
| 194 | i-Pen | H | H | Cl | 3-OCH$_2$—⟨phenyl⟩—CF$_3$ |
| 195 | i-Pen | Me | H | Cl | 4-OCH$_2$—⟨phenyl⟩ |
| 196 | i-Pen | Et | H | Br | 3-OCF$_2$CF$_3$ |
| 197 | n-Hex | H | H | Cl | 2-F |
| 198 | n-Hex | H | H | Cl | 4-Et |
| 199 | n-Hex | H | H | Cl | 2-OCH$_2$—⟨2,6-diF-phenyl⟩ |
| 200 | n-Hex | H | H | Cl | 4-OCH$_2$—⟨phenyl⟩—CN |

TABLE 2-continued

Compounds of the formula I:

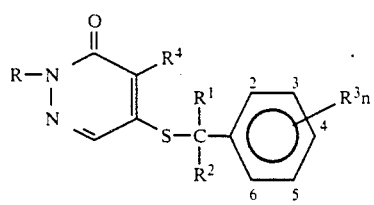

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | R¹ | R² | R⁴ | R³n |
|---|---|---|---|---|---|
| 201 | n-Hex | H | H | Cl | 4—⬡—H (cyclohexyl) |
| 202 | n-Hex | Me | H | Cl | 4-CN |
| 203 | n-Hex | Me | H | Cl | 2-NO₂ |
| 204 | n-Hex | Et | Me | Cl | 4-F |
| 205 | n-Hex | Et | Me | Cl | 4-OCH₂—⬡—H |
| 206 | n-Hex | H | H | Br | 4-CF₃ |
| 207 | n-Hex | H | H | Br | 3-OCF₃ |
| 208 | n-Hex | H | H | Br | 4-OCH₂—⬡(2,6-Cl₂) |
| 209 | n-Hex | Me | H | Br | 4—⬡ |
| 210 | n-Hex | Me | H | Br | 3-OCF₃ |
| 211 | n-Hex | Me | H | Br | 4-Cl |
| 212 | n-Hex | Et | H | Br | 2-Me |
| 213 | n-Hex | Et | Me | Br | 2,4-(Me)₂ |
| 214 | n-Hex | Et | Et | Br | 3,4-Cl₂ |
| 215 | n-Hex | Et | Et | Br | 4-OCH₂—⬡—Cl |
| 216 | Et | H | H | Cl | 4-O—⬡—CF₃ |
| 217 | Et | H | H | Cl | 2-O—⬡—NO₂ |
| 218 | Et | H | H | Cl | 2-Cl, 4-O—⬡(2,6-Cl₂) |

TABLE 2-continued

Compounds of the formula I:

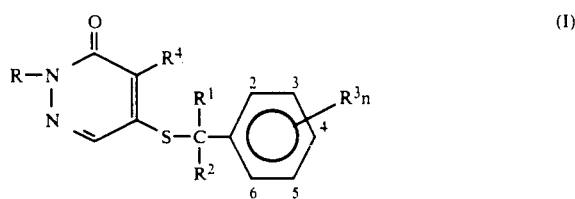

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3{}_n$ |
|---|---|---|---|---|---|
| 219 | Et | H | H | Cl | 2,6-Cl$_2$, 3-O—⟨phenyl⟩—CF$_3$ |
| 220 | Et | Et | Me | Br | 2-S—⟨phenyl⟩ |
| 221 | i-Pr | H | H | Br | 2-Cl, 4-O—⟨phenyl⟩—CN |
| 222 | i-Pr | Me | Me | Br | 4-S—⟨phenyl⟩—Cl |
| 223 | i-Pr | H | H | Cl | 4-O—⟨phenyl⟩—NO$_2$ |
| 224 | i-Pr | H | H | Cl | 4-O—⟨phenyl⟩—CF$_3$ |
| 225 | i-Pr | Me | H | Cl | 3-O—⟨phenyl⟩—Me |
| 226 | n-Pr | Me | H | Br | 4-O—⟨phenyl⟩—F |
| 227 | n-Pr | H | H | Cl | 4-O—⟨phenyl⟩—CF$_3$ |
| 228 | n-Pr | Et | H | Cl | 2-O—⟨phenyl⟩ |

TABLE 2-continued

Compounds of the formula I:

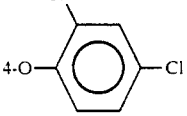

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3$n |
|---|---|---|---|---|---|
| 229 | i-Bu | n-Pr | H | Br | 4-O—⟨Cl, Cl⟩ |
| 230 | i-Bu | Me | H | Br | 4-O—⟨F⟩ |
| 231 | n-Bu | H | H | Br | 2-Cl, 4-O—⟨NO$_2$⟩ |
| 232 | n-Bu | H | H | Cl | 3-O—⟨Cl, Me⟩ |
| 233 | n-Bu | H | H | Cl | 4-O—⟨F⟩ |
| 234 | n-Bu | H | H | Cl | 4-O—⟨⟩ |
| 235 | s-Bu | H | H | Cl | 4-O—⟨cyclopropyl⟩ |
| 236 | t-Bu | H | H | Cl | 3-O—⟨Bu-t⟩ |
| 237 | t-Bu | Me | Me | Br | 2,6-Cl$_2$, 4-O—⟨Cl⟩ |
| 238 | t-Bu | H | H | Br | 3-O—⟨⟩ |

TABLE 2-continued

Compounds of the formula I:

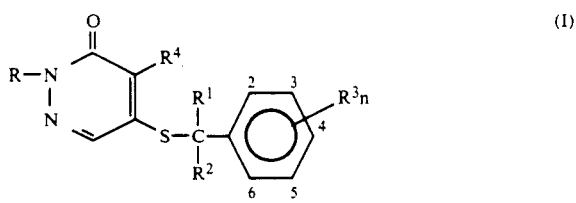

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 239 | t-Bu | Et | H | Br | 4-O–⟨⟩–F |
| 240 | t-Bu | H | H | Br | 4-O–⟨⟩ |
| 241 | t-Bu | Me | Me | Br | 4-O–⟨⟩ |
| 242 | t-Bu | H | H | Cl | 4-O–⟨⟩ |
| 243 | t-Bu | H | H | Cl | 4-O–⟨⟩–CF₃ |
| 244 | t-Bu | H | H | Cl | 4-O–⟨⟩(Cl)–CF₃ |
| 245 | t-Bu | Me | H | Cl | 4-O–⟨⟩–Bu-t |
| 246 | t-Bu | H | H | Cl | 4-O–⟨⟩–Cl |
| 247 | t-Bu | H | H | Cl | 4-O–⟨⟩–F |
| 248 | t-Bu | H | H | Cl | 4-S–⟨⟩(Cl)–CF₃ |

TABLE 2-continued

Compounds of the formula I:

(I)

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|-----|-----|-----|-----|-----|-----|
| 249 | t-Bu | H | H | Cl | 4-S-phenyl |
| 250 | i-Pen | H | H | Cl | 3-O-phenyl |
| 251 | i-Pen | H | H | Cl | 3-Cl, 4-O-(2-Cl, 4-CF$_3$-phenyl) |
| 252 | i-Pen | Me | H | Cl | 2,4-Cl$_2$, 4-O-(4-CN-phenyl) |
| 253 | i-Pen | Et | Me | Br | 2-O-phenyl |
| 254 | i-Pen | Me | Me | Cl | 4-O-(4-Br-phenyl) |
| 255 | i-Pen | Et | Et | Br | 3-O-phenyl |
| 256 | n-Pen | H | H | Cl | 3-O-phenyl |
| 257 | n-Hex | H | H | Cl | 4-O-(4-CF$_3$-phenyl) |
| 258 | n-Hex | H | H | Cl | 2-Cl, 4-S-(4-Br-phenyl) |
| 259 | n-Hex | H | H | Br | 3,5-Cl$_2$, 4-O-(4-CF$_3$-phenyl) |

TABLE 2-continued

Compounds of the formula I:

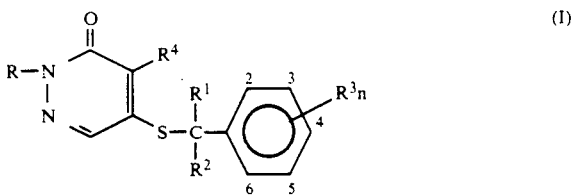

[In Table 2, "Me" denotes methyl, "Et" denotes ethyl, "Pr" denotes propyl, "Bu" denotes butyl, "Pen" denotes pentyl, "Hex" denotes hexyl, "n" denotes normal, "t" denotes tertiary, "i" denotes iso, and "s" denotes secondary.]

| No. | R | $R^1$ | $R^2$ | $R^4$ | $R^3n$ |
|---|---|---|---|---|---|
| 260 | t-Bu | H | H | Cl | 4-O–⟨phenyl⟩–CH$_2$Cl |

The compounds of the formula I can be produced by reacting a compound of the formula IIA:

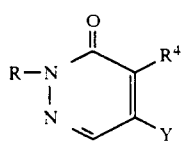

wherein R and $R^4$ have the same meanings as defined in formula I, and Y denotes —SH, a halogen or —OR$^5$ (wherein R$^5$ denotes a lower alkyl) with a compound of the formula IIIA:

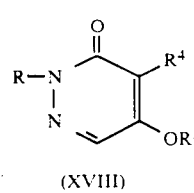

wherein $R^1$, $R^2$, $R^3$ and n have the same meanings as defined in formula I, and Z denotes a halogen or —SH, provided that Z denotes a halogen when Y is —SH and Z denotes —SH when Y is a halogen or —OR$^5$.

Specifically, the compounds of the present invention can be produced according to the following Reaction (1), (2) or (3):

Reaction (1):

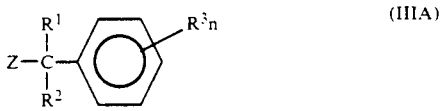

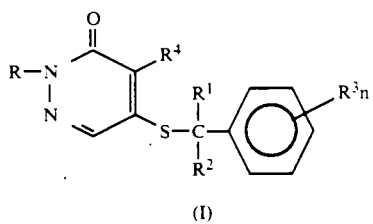

Reaction (2):

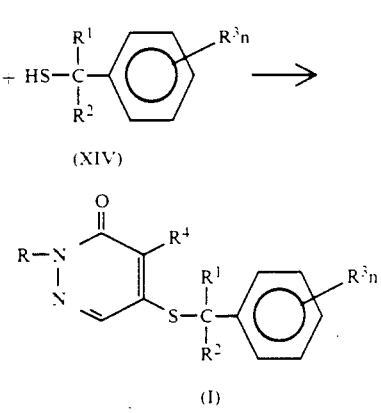

Reaction (3):

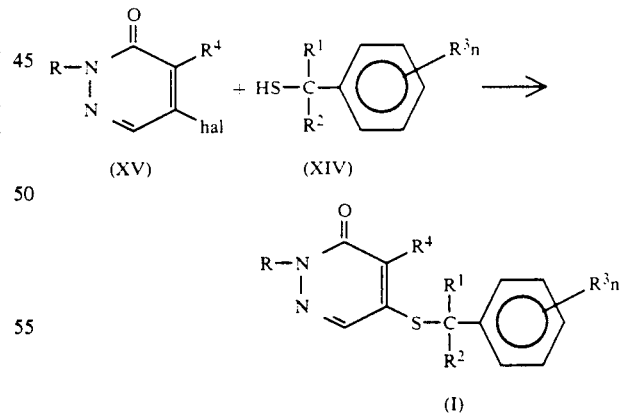

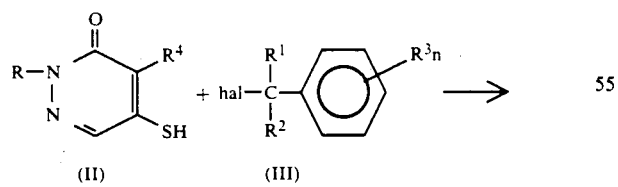

wherein R, $R^1$, $R^2$, $R^3$, $R^4$ and n in the above Reactions (1) through (3) have the same meanings as defined above, hal denotes a halogen and $R^5$ denotes a lower alkyl.

Namely, the compounds of the invention can be produced by reacting a 3(2H)-pyridazinone derivative of the formula II, XVIII or XV as one of the raw materials with a benzyl compound of the formula III or XIV as the other material in an appropriate solvent in the presence of a hydrogen halide-absorbing agent or an alcohol-removing agent.

As the solvent can be used lower alcohols such as methanol, ethanol; ketones such as acetone, methylethyl keton; hydrocarbons such as benzene, toluene; ethers such as isopropyl ether, tetrahydrofuran, 1,4-dioxane; amides such as N,N-dimethylformamide, hexamethyl phosphoric triamide; and halogenated hydrocarbons such as dichloromethane. As necessary, these solvents can be used as a mixture with water.

As the hydrogen halide-absorbing agent can be used inorganic bases such as sodium hydroxide, potassium hydroxide, sodium carbonate, potassium carbonate, sodium bicarbonate; and organic bases such as triethylamine, pyridine. As necessary, there may be added to the reaction system a catalyst such as tetraammonium salts (e.g. triethylbenzylammonium chloride).

The reaction temperature ranges from room temperature to the boiling point of the solvent to be used in the reaction.

The ratio of the raw materials can be optionally selected. However, it is advantageous to conduct the reaction using equimolar or nearly equimolar amount of the materials.

Incidentally, the compounds of the formula II in the above can be prepared by a process according to the following reaction:

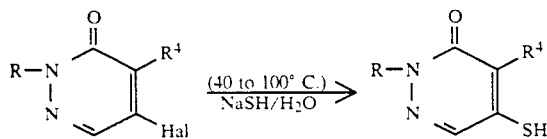

wherein R, R⁴ and Hal have the same meanings as defined above.

Preparation of the compounds I of the invention is described more in detail by way of the following examples which are not to restrict the invention.

SYNTHESIS EXAMPLE 1

Synthesis of 2-tert.-butyl-4-chloro-5-mercapto-3(2H)-pyridazinone

To 560 ml of water were added 66.3 g of 2-tert.-butyl-4,5-dichloro-3(2H)-pyridazinone and 48.0 g of 70% sodium hydrosulfide. After stirring at 60° C. for 4 hours activated carbon was added thereto. The resulting mixture was allowed to cool and then filtered. Concentrated hydrochloric acid was added to the resulting filtrate until the pH thereof was lowered to 2 or less. The resulting solid was filtered off, washed with water, dried and then recrystallized from a mixed solvent of benzene and n-hexane to give the intended product as white needle-like crystals of m.p. 112°–113° C. (yield: 81.5%).

The compound thus obtained was analyzed by means of ¹H-NMR spectrum in deutero chloroform (CDCl₃) to obtain the following results:

¹H-NMR(CDCl₃), δ(ppm): 1.61(9H,s,2-t-Bu), 4.04(1H,s,—SH), 7.56(1H,s,6—H).

SYNTHESIS EXAMPLE 2

Synthesis of 2-tert.-butyl-4-bromo-5-mercapto-3(2H)-pyridazinone

To 200 ml of water were added 31.0 g of 2-tert.-butyl-4,5-dibromo-3(2H)-pyridazinone and 15.8 g of 70% sodium hydrosulfide. After stirring at 60° C. for 4 hours, the resulting mixture was allowed to cool to room temperature and incorporated with about 8 ml of concentrated hydrochloric acid to lower the pH of the liquid to not higher than 2. The resulting solid was filtered off, washed with water, dried and then recrystallized from benzene/n-hexane to give 8.0g of the intended product as white crystals of m.p. 107°–110° C. (yield: 30.4%).

The compound thus obtained was analyzed by means of ¹H-NMR spectrum in deutero chloroform (CDCl₃) to obtain the following results:

¹H-NMR(CDCl₃), δ(ppm): 1.63(9H,s,2-t-Bu), 4.18(1H,s,—SH), 7.53(1H,s,6-H).

SYNTHESIS EXAMPLE 3

Synthesis of 2-tert.-butyl-4-chloro-5-(2-methylbenzylthio)-3(2H)-pyridazinone (Compound No. 77)

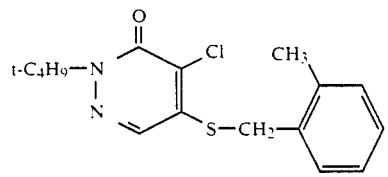

In 10 ml of N,N-dimethylformamide was dissolved 1.5 g of 2-tert.-butyl-4-chloro-5-mercapto-3(2H)-pyridazinone, and thereto were added 1.2 g of anhydrous potassium carbonate and 1.0 g of α-chloro-o-xylene. The resulting mixture was heated to 80 to 110° C. under stirring for 2 hours. After allowed to cool to room temperature, the mixture was incorporated with 100 ml of water and then stirred. The precipitated solid was filtered off, washed with water, dried and recrystallized from ethanol to give white needle-like crystals having the following physical properties (yield: 72.7%):

mp: 138.0°–139.0° C. ¹H-NMR(CDCl₃),δ(ppm): 1.62(9H,s,2-t-Bu), 2.40(3H,s,2′—CH₃), 4.21(2H,s,—SCH₂—), 7.18(4H,m, phenyl), 7.61(1H,s,6-H).

SYNTHESIS EXAMPLE 4

Synthesis of 2-tert.-butyl-4chloro-5-(4-tert.-butylbenzylthio)-3(2H)-pyridazinone (Compound No. 81)

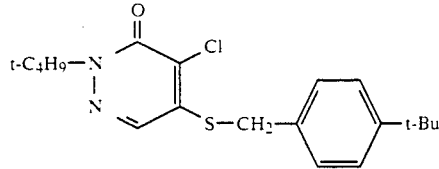

By conducting a procedure similar to that in Synthesis Example 3 except using 2.0 g of 2-tert.-butyl-4-chloro-5-mercapto-3(2H)-pyridazinone, 15 ml of N,N-dimethylformamide, 1.3 g of anhydrous sodium carbonate and 1.6 g of 4-tert.-butylbenzyl chloride, there were obtained white needle-like crystals having the following physical properties (yield: 87.9%):

m.p.: 111.0°–112.0° C.

¹H-NMR(CDCl₃), δ(ppm): 1.29(9H,s,4′-t-Bu), 1.60(9H,s,2-t-Bu), 4.21(2H,s,—SCH₂—), 7.32(4H,m, phenyl), 7.61(1H,s,6-H).

SYNTHESIS EXAMPLE 5

Synthesis of 2-tert.-butyl-4-chloro-5-(4-tert.-butyl-α-methylbenzylthio)-3(2H)-pyridazinone (Compound No. 70)

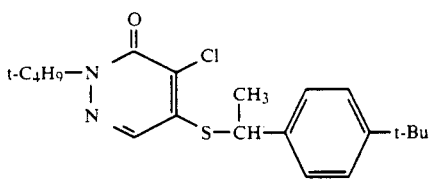

By conducting a procedure similar to that in Synthesis Example 3 except using 1.5 g of 2-tert.-butyl-4-chloro-5-mercapto-3(2H)-pyridazinone, 10 ml of N,N-dimethylformamide, 1.0 g of anhydrous sodium carbonate and 1.4 g of 4-tert.-butyl-α-methylbenzyl chloride, there were obtained white needlelike crystals having the following physical properties (yield: 72.7%):

m.p.: 100.0°–106.0° C.

1H-NMR(CDCl$_3$), δ(ppm): 1.29(9H,s,4'-t-Bu), 1.58(9H,s,2-t-Bu), 1.70(3H,d,J=7HZ, α—CH$_3$), 4.58(1H,q,—SCH<), 7.33(4H,m,phenyl), 7.56(1H,s,6-H).

SYNTHESIS EXAMPLE 6

Synthesis of (+)2-tert.-butyl-4-chloro-5-(4-tert.-butyl-α-methylbenzylthio)-3(2H)-pyridazinone (Compound No. 71)

In 300 ml of 0.2 M aqueous solution of disodium hydrogenphosphate (pH 9.1) was suspended 17.0 g (77.2m mol) of p-tert.-butyl-α-methylbenzyl acetate, and 1.00 g of bovin liver acetone powder was added thereto. After stirring at room temperature for 77 hours, the reaction liquid was extracted twice with 200 ml each of ethyl acetate (insoluble matter was removed by means of Celite filtration). The ethyl acetate layer was dried over anhydrous sodium sulfate and freed of solvent by distillation to give 16.1 g of almost colorless oily residue.

The oily residue was fractionated on silica gel column chromatography [developer: a benzene/ethyl acetate 20/1 (V/V) mixture] to obtain 3.60 g of (+)-p-tert.-butyl-α-methylbenzyl alcohol as colorless crystals having a melting point of 85° C. (yield: 26.2%); $[\alpha]_D^{25}$+47.8° (C=1.01, C$_6$H$_{12}$), 98% e.e.

A part of the product (3.49 g) was recrystallized from 10.5 g of hexane to obtain 3.06 g of crystals of 100% e.e., $[\alpha]_d^{25}$+48.9° (C=1.03, C$_6$H$_{12}$).

Also, was obtained 12.16 g of (−)-p-tert.-butyl-α-methylbenzyl acetate as an almost colorless oil (yield: 71.5%) of $[\alpha]_D^{25}$−36.9° (C=1.09, C$_6$H$_{12}$), 35.6% e.e.

To 25 ml of ethyl ether were added 1.78 g of (+)-4-tert.-butyl-α-methylbenzyl alcohol of 100% e.e. and 1.8 g of dry pyridine. The resulting mixed solution was kept at −25° C. and added dropwise with a solution of 3.1 g of phosphorus tribromide dissolved in 18 ml of ethyl ether (at −15° to −25° C.). After completion of addition, the resulting mixture was stirred at −10° C. for one hour and then allowed to stand at 5° C. for 2 days. Ice water was added thereto. The resulting organic layer was washed successively with a saturated aqueous solution of sodium bicarbonate and with ice water, dried with anhydrous Glauber's salt, and freed of solvent by distillation under reduced pressure to give 1.6 g of 4-tert.-butyl-α-methylbenzyl bromide.

The resulting product 0.96 g was added to a mixed solution of 0.87 g of 2-tert.-butyl-4-chloro-5-mercapto-3(2H)-pyridazinone, 20 ml of hexamethyl phosphoric triamide and 0.25 g of anhydrous sodium carbonate at −20° C. The resulting mixture was allowed to stand for 2 days at room temperature. Then the mixture was incorporated with 300 ml of benzene and washed twice with water. The resulting organic layer was dried with anhydrous Glauber's salt, and freed of solvent by distillation to obtain a crude product. The crude product was purified by means of thin-layer chromatography (using a benzene/ethyl acetate.50/1 mixture, R$_f$=0.5). Hexane was added to 1.1 g of the product thus obtained to give 0.83 g of crystals.

The compound thus obtained was identical with that obtained in Synthesis Example 5 according to $^1$H-NMR measurement.

m.p.: 102.3°–104.3° C.

$[\alpha]_D^{25}$+0.96° (C=1.0, CHCl$_3$).

SYNTHESIS EXAMPLE 7

Synthesis of (−)2-tert.-butyl-4-chloro-5-(4-tert.-butyl-α-methylbenzylthio)-3(2H)-pyridazinone (Compound No. 72)

In 400 ml of 0.2 M aqueous solution of disodium hydrogenphosphate was suspended 22.6 g of (−)-p-tert.-butyl-α-methylbenzyl acetate of $[\alpha]_D^{25}$−36.9° (C=1, C$_6$H$_{12}$) and optical purity 35.6% e.e. obtained in Synthesis Example 6, and 1.33 g of chicken liver acetone powder was added thereto. The resulting mixture was subjected to reaction at 25° C. for 67 hours. The reaction liquid was extracted twice with 400 ml each of ethyl acetate (insoluble matter was removed by Celite filtration). The ethyl acetate layer was dried over anhydrous sodium sulfate and freed of solvent by distillation. The resulting pale yellow oily residue was subjected to column chromatography (on 200 g of silica gel, wherein p-tert.-butyl-α-methylbenzyl acetate was eluted with a benzene/ethyl acetate 50/1 (V/V) mixture and then p-tert.-butyl-α-methylbenzyl alcohol was eluted with benzene/ethyl acetate 10/1 (V/V) mixture and, thereafter, the solvent in each elute was distilled away). Thus were obtained 14.01 g (yield: 62%) of (−)-p-tert.-butyl-α-methylbenzyl acetate of $[\alpha]_D^{25}$−85.5° (C=1.07, C$_6$H$_{12}$), optical purity 82.6% e.e. and 6.25 g (yield 34%) of (+)-p-tert.-butyl-α-methylbenzyl alcohol of $[\alpha]_D^{25}$+23.1° (C=1.07, C$_6$H$_{12}$), optical purity 47.2% e.e.

In 33.6 ml of methanol was dissolved 13.79 g (62.6 m mol) of (−)-p-tert.-butyl-α-methylbenzyl acetate of $[\alpha]_D^{25}$−85.5° (C=1.07, C$_6$H$_{12}$), optical purity 82.6% e.e. After the resulting solution was stirred and ice-cooled, 21.7 g of 15% aqueous solution of sodium hydroxide (sodium hydroxide 81.4 m mol) was added thereto dropwise over 5 minutes.

After the resulting mixture was allowed to cool to room temperature, it was stirred for one hour and then incorporated with 100 ml of water and 100 ml of benzene for extraction. The aqueous layer was extracted again with 30 ml of benzene. The benzene layers were combined, washed with water, dried over anhydrous sodium sulfate and freed of solvent by distillation to obtain 10.86 g (yield: 97%) of colorless (−)-p-tert.-butyl-α-methylbenzyl alcohol; $[\alpha]_D^{25}$−41.1° (C=1.03, C$_6$H$_{12}$), 84.0% e.e.

A portion (10.6 g) of the product was recrystallized from 31.8 g of hexane to obtain 8.20 g of (−)-p-tert.-butyl-α-methylbenzyl alcohol of $[\alpha]_D^{25}$−47.8° (C=1.00, C$_6$H$_{12}$), optical purity 97.8% e.e.

Then, procedure similar to that in Synthesis Example 6 was conducted. Namely, reaction and purification similar to those in Synthesis Example 6 was conducted except using 1.78 g of (−)-4-tert.-butyl-α-methylbenzyl alcohol (enantiomer of the product in Synthesis Example 6) having optical rotation (−) and optical purity 97.8% e.e. instead of 1.78 g of the (+) isomer thereof to obtain 0.62 g of crystals of the intended compound. The compound was identical with that obtained in Synthesis Example 5 according to $^1$H-NMR measurement.

m.p. 102.2°–106.7° C.

$[\alpha]_D^{25}$ −1.14° (C=1.0, CHCl$_3$).

SYNTHESIS EXAMPLE 8

Synthesis of 2-tert.-butyl-4-chloro-5-[4'-(4''-trifluoromethyl-phenoxy)benzylthio]-3(2H)-pyridazinone (Compound No. 243)

In 30 ml of N,N-dimethylformamide were dissolved 2.2 g (0.01 mol) of 2-tert.-butyl-4-chloro-5-mercapto-3(2H)-pyridazinone and 3.5 g (0.0105 mol) of 4-(4'-trifluoromethylphenoxy) benzyl bromide, and thereto was added 2.1 g (0.02 mol) of anhydrous sodium carbonate to effect reaction at 85° to 90° C. for 4 hours. After the reaction, the reaction liquid was allowed to cool, poured into water and then extracted with benzene. The benzene layer was washed with 5% aqueous solution of sodium hydroxide and then with water, dried over anhydrous sodium sulfate and then freed of benzene by distillation under reduced pressure. The oily residue was incorporated with n-hexane and the precipitated crystals were filtered off to obtain white crystals (yield: 85.5%).

m.p. 152.0°–155.5° C.

$^1$H-NMR(CDCl$_3$), δ(ppm): 1.60(9H,s,2-t-Bu), 4.22(2H,s,—SCH$_2$—), 6.92–7.60(9H,m, phenyl and 6-H).

SYNTHESIS EXAMPLE 9

Synthesis of 2-tert.-butyl-4-bromo-5-(4-tert.-butyl-benzylthio)-3(2H)-pyridazinone (Compound No. 139)

To a dimethylformamide solution of 4.4 g of 2-tert.-butyl-4-bromo-5-mercapto-3(2H)-pyridazinone and 4.7 g of 4-tert.-butylbenzyl bromide was added 3.5 g of sodium carbonate. The resulting reaction liquid was stirred at 80° C. for 4 hours, allowed to cool to room temperature, incorporated with water and extracted with benzene. The benzene layer was washed with 3% aqueous solution of sodium hydroxide and then with water, dried and then freed of benzene by distillation to give yellowish brown solid. The solid was recrystallized from a mixed solvent of benzene and n-hexane to obtain white crystals (yield: 64%).

m.p. 137.0°–139.0° C.

$^1$H-NMR(CDCl$_3$), δ(ppm): 1.33(9H,s,4'-t-Bu), 1.62(9H,s,2-t-Bu), 4.21(2H,s,—SCH$_2$—), 7.33(4H,m, phenyl), 7.54(1H,s,6-H).

SYNTHESIS EXAMPLE 10

Synthesis of 2-tert.-butyl-4-chloro-5-(4-tert.-butyl-benzylthio)-3(2H)-pyridazinone (Compound No. 81)

A mixture of 1.5 g of 2-tert.-butyl-4-chloro-5-mercapto-3(2H)-pyridazinone, 200 ml of benzene, 1.5 g of anhydrous potassium carbonate and 1.4 g of 4-tert.-butylbenzyl chloride was subjected to reaction at a reflux temperature for 6 hours. Then, procedure similar to that in Synthesis Example 5 was conducted to obtain white crystals (yield: 60%).

The compound thus obtained was identical with that obtained in Synthesis Example 4 according to $^1$H-NMR measurement.

SYNTHESIS EXAMPLE 11

Synthesis of 2-tert.-butyl-4-chloro-5-(4-chlorobenzylthio)-3(2H)-pyridazinone (Compound No. 175)

Sodium hydroxide 0.7 g was dissolved in 15 ml of water, and thereto were added 100 ml of benzene, 3.3 g of 2-tert.- butyl-4,5-dichloro-3(2H)-pyridazinone and 0.15 g of triethylbenzylammonium chloride. The resulting solution was incorporated with 2.4 g of 4-chlorobenzyl mercaptan at room temperature and then stirred for 15 hours. After completion of the reaction, only the organic layer was separated therefrom, washed with a 5% aqueous solution of sodium hydroxide and then with water, and dried over anhydrous sodium sulfate. Solvent was distilled away therefrom under reduced pressure. The resulting oily residue was incorporated with hexane to give crystals. The crystals were filtered off to obtain 3.3 g of the intended compound (yield: 64%).

m.p. 142.0°–143.0° C.

$^1$H-NMR(CDCl$_3$), δ(ppm): 1.60(9H,s,t-Bu), 4.20(2H,s,—SCH$_2$—), 7.32(4H,s, phenyl), 7.56(1H,s,6-H).

SYNTHESIS EXAMPLE 12

Synthesis of 2-tert.-butyl-4-bromo-5-(4-tert.-butyl-benzylthio)-3(2H)-pyridazinone (Compound No. 139)

Sodium hydroxide 0.22 g was dissolved in 5 ml of water, and thereto were added 10 ml of dichloromethane, 1.55 g of 2-tert.-butyl-4,5-dibromo-3(2H)-pyridazinone and 0.05 g of triethylbenzylammonium chloride. The resulting solution was incorporated with 0.83 g of 4-tert.-butyl-benzyl mercaptan at room temperature and then stirred for 10 hours. After completion of the reaction, about 50 ml of CH$_2$Cl$_2$ was added to the solution and the organic layer was separated therefrom, washed with a 5% aqueous solution of sodium hydroxide and then with water, and dried over anhydrous sodium sulfate. Solvent was distilled away therefrom under reduced pressure and the resulting solid residue was recrystallized from a benzene/n-hexane mixed solvent to obtain 1.32 g of the intended compound (yield: 65%).

m.p. 137.0°–139.0° C.

$^1$H-NMR(CDCl$_3$), δ(ppm): 1.33(9H,s,t-Bu), 1.62(9H,s,t-Bu), 4.21(2H,s,—SCH$_2$—), 7.33(4H,s. phenyl), 7.54(1H,s,6-H).

SYNTHESIS EXAMPLE 13

Synthesis of 2-tert.-butyl-4-chloro-5-(4-tert.-butyl-benzylthio-3(2H)-pyridazinone (Compound No. 81)

Sodium hydroxide 0.7 g was dissolved in 15 ml of water and thereto were added 30 ml of dichloromethane, 3.3 g of 2-tert.-butyl-4,5-dichloro-3(2H)-pyridazinone and 0.15 g of triethylbenzylammonium chloride. The resulting solution was incorporated with 2.7 g of 4-tert.-butylbenzyl mercaptan at room temperature and then stirred for 15 hours. After completion of the reaction, only the organic layer was separated therefrom, washed with a 5% aqueous solution of sodium hydroxide and then with water, and dried over anhydrous sodium sulfate. Solvent was distilled away therefrom under reduced pressure and the resulting oily residue was incorporated with hexane to give crystals. The crystals were filtered off to obtain 3.8 g of the intended compound (yield: 70%).

The physical properties of the compound were identical with those of the product of Synthesis Example 4.

The compounds produced according to one of the processes in Synthesis Examples 3 through 10 are listed in Table 3 below.

Incidentally, the compounds produced in Synthesis Examples 3 through 10 are also included in Table 3.

TABLE 3

The compounds of the formula I:

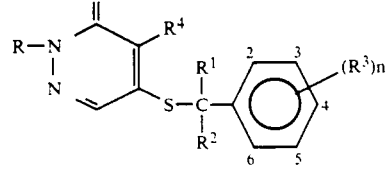

(I)

[In Table 3, "Me" denotes methyl, "Et" denotes ethyl, "Pr" denotes propyl, "Bu" denotes butyl, "n" denotes normal, "t" denotes tertiary, "i" denotes iso and "s" denotes secondary.]

| Compound No. | R | R$^1$ | R$^2$ | R$^4$ | R$^3$n | M.P. (°C.) |
|---|---|---|---|---|---|---|
| 1 | Et | H | H | Cl | 4-t-Bu | 123.0–124.5 |
| 2 | Et | H | H | Cl | 4-F | 106.0–108.5 |
| 4 | Et | H | H | Cl | 4-phenyl | 140.0–143.0 |
| 14 | n-Pr | H | H | Cl | 4-t-Bu | 159.0–161.0 |
| 29 | i-Pr | H | H | Cl | 3,4-Cl$_2$ | 181.0–187.0 |
| 30 | i-Pr | H | H | Cl | 4-t-Bu | 141.0–142.0 |
| 70 | t-Bu | Me | H | Cl | 4-t-Bu | 100.0–106.0 |
| 71 | optically active compound (+) of Compound No. 70 | | | | | 102.3–104.3 |
| 72 | optically active compound (−) of Compound No. 70 | | | | | 102.2–106.7 |
| 73 | t-Bu | H | H | Cl | 4-O-(6-chloroquinoxalin-2-yl) | 170.0–176.0 |
| 74 | t-Bu | H | H | Cl | 4-O-(6-CF$_3$-quinoxalin-2-yl) | 169.1–171.5 |
| 75 | t-Bu | H | H | Cl | 4-O-(3-CF$_3$-pyridin-2-yl) | 112.1–113.5 |
| 76 | t-Bu | H | H | Cl | 4-O-(quinoxalin-2-yl) | 198.2–199.6 |
| 77 | t-Bu | H | H | Cl | 2-Me | 138.0–139.0 |
| 78 | t-Bu | H | H | Cl | 3-Me | 86.5–87.5 |
| 79 | t-Bu | H | H | Cl | 4-Me | 119.0–120.0 |
| 80 | t-Bu | H | H | Cl | 4-i-Pr | 96.5–98.0 |
| 81 | t-Bu | H | H | Cl | 4-t-Bu | 111.0–112.0 |
| 84 | t-Bu | H | H | Cl | 3,4-Cl$_2$ | 111.0–112.0 |
| 87 | t-Bu | H | H | Cl | 4-F | 112.5–114.0 |

TABLE 3-continued

The compounds of the formula I:

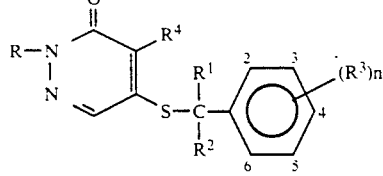

(I)

[In Table 3, "Me" denotes methyl, "Et" denotes ethyl, "Pr" denotes propyl, "Bu" denotes butyl, "n" denotes normal, "t" denotes tertiary, "i" denotes iso and "s" denotes secondary.]

| Compound No. | R | R¹ | R² | R⁴ | R³n | M.P. (°C.) |
|---|---|---|---|---|---|---|
| 88 | t-Bu | H | H | Cl | 4—cyclohexyl (H) | 157.0–159.0 |
| 95 | t-Bu | H | H | Cl | 4—phenyl | 169.0–171.0 |
| 97 | t-Bu | H | H | Cl | 4-Br | 144.0–146.0 |
| 101 | t-Bu | Me | H | Cl | 3-Me | 118.0–119.0 |
| 102 | t-Bu | Me | H | Cl | 4-Me | 83.0–84.0 |
| 103 | t-Bu | Me | H | Cl | 4-i-Pr | 73.0–74.5 |
| 104 | t-Bu | H | H | Cl | 4-O—(3-Cl, 5-CF₃-pyridyl) | 129.0–131.0 |
| 106 | t-Bu | Me | H | Cl | 4—cyclohexyl (H) | 102.0–104.0 |
| 107 | t-Bu | Me | H | Cl | 4-Br | 122.5–123.5 |
| 108 | t-Bu | Me | H | Cl | 4-Cl | 98.5–99.5 |
| 109 | t-Bu | Me | H | Cl | 4—phenyl | 140.0–142.0 |
| 110 | t-Bu | Et | H | Cl | 4-t-Bu | oil |
| 112 | t-Bu | H | H | Cl | 2-NO₂ | 121.0 |
| 115 | t-Bu | Et | H | Cl | 4-Cl | oil |
| 126 | t-Bu | H | H | Cl | 4-OCH₂—C₆H₄—Cl | 143.0–146.0 |
| 127 | t-Bu | H | H | Cl | 4-OCH₂—C₆H₄—Me | 120.0–122.2 |
| 128 | t-Bu | H | H | Cl | 4-OCH₂—C₆H₄—Me (2-Me) | 110.0–111.0 |
| 129 | t-Bu | H | H | Cl | 4-OCH₂CH=CH₂ | 59.0–68.0 |
| 130 | t-Bu | H | H | Cl | 4-SC₄H₉-n | oil |
| 131 | t-Bu | H | H | Cl | 4-SMe | semi solid |

TABLE 3-continued

The compounds of the formula I:

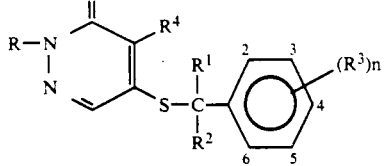

(I)

[In Table 3, "Me" denotes methyl, "Et" denotes ethyl, "Pr" denotes propyl, "Bu" denotes butyl, "n" denotes normal, "t" denotes tertiary, "i" denotes iso and "s" denotes secondary.]

| Compound No. | R | $R^1$ | $R^2$ | $R^4$ | $R^3n$ | M.P. (°C.) |
|---|---|---|---|---|---|---|
| 132 | t-Bu | H | H | Cl | 3-OC$_4$H$_9$-n | semi solid |
| 133 | t-Bu | H | H | Cl | 4-Si(Me)$_3$ | 99.6–101.4 |
| 134 | t-Bu | Me | H | Cl | 4-C$_6$H$_4$-Cl | 149.0–150.0 |
| 135 | t-Bu | Me | H | Cl | 4-C$_6$H$_4$-Me | 118.0–120.0 |
| 136 | t-Bu | H | H | Cl | 4-SCHF$_2$ | 77.0–77.5 |
| 137 | t-Bu | H | H | Cl | 4-OCH$_2$CH$_2$CH$_2$Cl | semi solid |
| 138 | t-Bu | H | H | Cl | 4-OCHF$_2$ | 75.0–78.0 |
| 139 | t-Bu | H | H | Br | 4-t-Bu | 137.0–139.0 |
| 140 | t-Bu | H | H | Br | 4-Cl | 163.0–165.0 |
| 141 | t-Bu | H | H | Cl | 4-cyclopropyl(H) | 68.0–68.3 |
| 142 | t-Bu | H | H | Cl | 4-C(Me)$_2$CH$_2$Cl | 127.0–129.0 |
| 143 | t-Bu | H | H | Cl | 4-OCHC(Me)=CH$_2$ | 98.6–100.0 |
| 144 | t-Bu | H | H | Cl | 3,5-(t-Bu)$_2$, 4-OH | 164.7–166.3 |
| 145 | t-Bu | H | H | Cl | 3,5-(Br)$_2$, 4-OH | 191.7–193.4 |
| 146 | t-Bu | H | H | Br | 4-cyclohexyl(H) | 147.0–152.0 |
| 147 | t-Bu | H | H | Br | 4-n-C$_4$H$_9$ | 84.0–86.0 |
| 148 | t-Bu | H | H | Br | 4-OC$_6$H$_{13}$-n | 71.0–73.0 |
| 149 | t-Bu | Me | H | Br | 4-C$_6$H$_5$ | Oil |
| 150 | t-Bu | H | H | Cl | 4-N(Me)$_2$ | 136.5–140.0 |
| 151 | t-Bu | H | H | Cl | 3-OMe, 4-OPr-i | 86.0–88.0 |
| 152 | t-Bu | H | H | Cl | 4-I | 117.0–118.0 |
| 153 | t-Bu | H | H | Cl | 4-OEt | 90.0–91.0 |
| 154 | t-Bu | H | H | Cl | 4-OC$_3$H$_7$-n | 105.0–106.0 |
| 155 | t-Bu | H | H | Cl | 4-i-Bu | 125.0–129.0 |
| 156 | t-Bu | H | H | Cl | 4-n-Bu | 92.0–94.0 |
| 157 | t-Bu | H | H | Cl | 4-n-C$_6$H$_{13}$ | 104.0–106.0 |
| 158 | t-Bu | H | H | Cl | 4-n-C$_7$H$_{15}$ | semi solid (4-position 80%, 2-position 20%) |
| 159 | t-Bu | H | H | Cl | 4-n-C$_8$H$_{17}$ | 55.0–65.0 (4-position 70%, 2-position 30%) |
| 160 | t-Bu | H | H | Cl | 4-sec.-Bu | 95.0–97.0 |
| 161 | t-Bu | H | H | Cl | 4-t-C$_5$H$_{11}$ | 142.0–143.0 |
| 162 | t-Bu | H | H | Cl | 4-COOMe | 117.0–122.0 |
| 163 | t-Bu | H | H | Cl | 4-OPr-i | 131.0–132.5 |
| 164 | t-Bu | H | H | Cl | 4-OCH$_2$CH(Et)Bu-n | oil |
| 165 | t-Bu | H | H | Cl | 4-OC$_9$H$_{19}$-n | oil |
| 166 | t-Bu | H | H | Cl | 4-OC$_{11}$H$_{23}$-n | oil |

TABLE 3-continued

The compounds of the formula I:

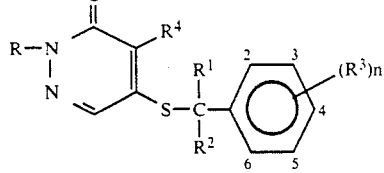

(I)

[In Table 3, "Me" denotes methyl, "Et" denotes ethyl, "Pr" denotes propyl, "Bu" denotes butyl, "n" denotes normal, "t" denotes tertiary, "i" denotes iso and "s" denotes secondary.]

| Compound No. | R | R$^1$ | R$^2$ | R$^4$ | R$^3$n | M.P. (°C.) |
|---|---|---|---|---|---|---|
| 167 | t-Bu | Me | H | Cl | 4-OC$_{10}$H$_{21}$-n | oil |
| 168 | t-Bu | H | H | Cl | 4-OC$_4$H$_9$-n | 89.0–89.5 |
| 169 | t-Bu | H | H | Cl | 4-OC$_5$H$_{11}$-n | 88.0–88.5 |
| 170 | t-Bu | H | H | Cl | 4-OC$_6$H$_{13}$-n | 85.0–86.0 |
| 171 | t-Bu | H | H | Cl | 4-OC$_7$H$_{15}$-n | 77.0–78.0 |
| 172 | t-Bu | H | H | Cl | 4-OC$_8$H$_{17}$-n | 64.0–66.0 |
| 173 | t-Bu | H | H | Cl | 2,6-(Me)$_2$, 4-t-Bu | 207.0–208.5 |
| 174 | t-Bu | H | H | Cl | 3,5-Br$_2$, 4-OPr-i | 46.0–48.0 |
| 175 | t-Bu | H | H | Cl | 4-Cl | 142.0–143.0 |
| 176 | t-Bu | H | H | Cl | 4-CF$_3$ | 125.0–127.0 |
| 177 | t-Bu | H | H | Cl | 4-OCH$_2$-(2-Cl-phenyl) | 132.0–133.0 |
| 178 | t-Bu | H | H | Cl | 4-CH$_2$-phenyl | oil |
| 179 | t-Bu | H | H | Cl | 4-OCH(Me)COOEt | 111.0–113.0 |
| 180 | t-Bu | H | H | Cl | 4-OCH$_2$CH=CH—Me | 64.0–66.0 |
| 181 | t-Bu | H | H | Cl | 4-SCN | 104.5–109.0 |
| 216 | Et | H | H | Cl | 4-O-(4-CF$_3$-phenyl) | 127.0–131.0 |
| 224 | i-Pr | H | H | Cl | 4-O-(4-CF$_3$-phenyl) | 133.0–135.0 |
| 227 | n-Pr | H | H | Cl | 4-O-(4-CF$_3$-phenyl) | 137.0–140.0 |
| 243 | t-Bu | H | H | Cl | 4-O-(4-CF$_3$-phenyl) | 152.0–155.5 |
| 244 | t-Bu | H | H | Cl | 4-O-(2-Cl, 4-CF$_3$-phenyl) | 109.0–110.0 |
| 245 | t-Bu | Me | H | Cl | 4-O-(4-Bu-t-phenyl) | oil |

TABLE 3-continued

The compounds of the formula I:

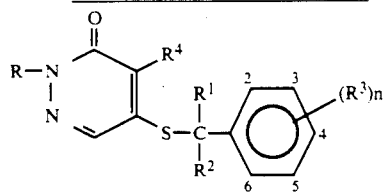

[In Table 3, "Me" denotes methyl, "Et" denotes ethyl, "Pr" denotes propyl, "Bu" denotes butyl, "n" denotes normal, "t" denotes tertiary, "i" denotes iso and "s" denotes secondary.]

| Compound No. | R | $R^1$ | $R^2$ | $R^4$ | $R^3$n | M.P. (°C.) |
|---|---|---|---|---|---|---|
| 246 | t-Bu | H | H | Cl | 4-O—⟨◯⟩—Cl | 146.0–147.0 |
| 249 | t-Bu | H | H | Cl | 4-S—⟨◯⟩ | oil |
| 260 | t-Bu | H | H | Cl | 4-O—⟨◯⟩—CH₂Cl | oil ($n_D^{20}$ 1.6073) |

When the compounds according to the present invention are used for insecticidal, acaricidal, nematicidal and/or fungicidal agents for agricultural and horticultural uses or for expellents of ticks parasitic on animals, they are generally mixed with appropriate carriers, for instance, solid carriers such as clay, talc, bentonite or diatomaceous earth, or liquid carriers such as water, alcohols (e.g. methanol and ethanol), aromatic hydrocarbons (e.g. benzene, toluene and xylene), chlorinated hydrocarbons, ethers, ketones, acid amides (e.g. dimethylformamide) or esters (e.g. ethyl acetate). If desired, to these mixtures may be added emulsifier, dipersing agent, suspension agent, penetrating agent, spreader, stabilizer and the like to put them into practical uses in the form of liquid preparation, emulsifiable concentrate, wettable powder, dust, granule, flowable or the like. Moreover, the mixtures may be incorporated with other herbicides, various insecticides, fungicides, plant-growth regulating agents and/or synergists during preparation or application thereof, as necessary.

The amount of the compounds of the invention to be used as an active ingredient is suitably in the range of 0.005 to 5 kg per hectare although it varies depending upon the place and the season where the compounds are applied, manner of application, diseases and insect pests to be applied, cultivated crops to be protected and the like.

In the following, there are shown formulation examples of fungicidal, insecticidal, acaricidal and/or nematicidal compositions and expellent compositions for ticks parasitic on animals, said compositions containing the compounds of the present invention as an active ingredient. These examples are only illustrative and not to restrict the invention. In the following examples, "part" means "part by weight".

| Formulation Example 1: Emulsifiable concentrates | |
|---|---|
| Active ingredient | 25 parts |
| Xylene | 55 parts |
| N,N-dimethylformamide | 20 parts |
| Solpol 2680 (trade name, a mixture of a non-ionic surface-active agent and an anionic surface-active agent manufactured by Toho Chemicals. Co., Ltd., Japan) | 5 parts |

The above components are mixed intimately together to form an emulsifiable concentrate. Upon use, the emulsifiable concentrate is diluted with water up to one five hundredth to one twenty thousandth in concentration and applied at a rate of 0.005 to 5 kg of the active ingredient per hectare.

| Formulation Example 2: Wettable powders | |
|---|---|
| Active ingredient | 25 parts |
| Siegreit PFP (trade name, caoline-based clay manufactured by Siegreit Mining Industries Co., Ltd.) | 69 parts |
| Solpol 5039 (trade name, a mixture of a non-ionic surface-active agent and an anionic surface-active agent manufactured by Toho Chemical Co., Ltd., Japan) | 3 parts |
| Carplex (trade name, coagulation-inhibition agent, a mixture of a surface-active agent and white carbon manufactured by Shionogi Seiyaku K.K., Japan) | 3 parts |

The above components are homogeneously mixed together and ground to form a wettable powder. Upon use, the wettable powder is diluted with water up to one five hundredth to one twenty thousandth and applied at a rate of 0.995 to 5 kg of the active ingredient per hectare.

| Formulation Example 3: Oil solutions | |
|---|---|
| Active ingredient | 10 parts |
| methylcellosolve | 90 parts |

The above components are homogeneously mixed together to form an oil solution. Upon use, the oil solution is applied at a rate of 0.005 to 5 kg of the active ingredient per hectare.

| Formulation Example 4: Dusts | |
|---|---|
| Active ingredient | 3.0 parts |
| Carplex (trade name, coagulation-inhibition agent as mentioned in the above) | 0.5 parts |
| Clay | 95.0 parts |
| di-isopropyl phosphate | 1.5 parts |

The above components are homogeneously mixed together and ground to form a dust. Upon use, the dust is applied at a rate of 0.005 to 5 kg of the active ingredient per hectare.

| Formulation Example 5: Granules | |
|---|---|
| Active ingredient | 5 parts |
| Bentonite | 54 parts |
| Talc | 40 parts |
| Calcium lignin sulfonate | 1 part |

The above components are mixed intimately together and ground, incorporated with a small amount of water and mixed together with stirring. The resulting mixture is granulated by means of extrusion-granulator and dried to form granules. Upon use, the granule is applied at a rate of 0.005 to 5 kg of the active ingredient per hectare.

| Formulation Example 6: Flowables | |
|---|---|
| Active ingredient | 25 parts |
| Solpol 3353 (trade name, a non ionic surface-active agent manufactured by Toho Chemicals, Co., Ltd., Japan) | 10 parts |
| Runox 1000C (trade name, an anionic surface-active agent manufactured by Toho Chemicals, Co., Ltd., Japan) | 0.5 parts |
| 1% aqueous solution of Xanthan gum (natural high-molecular compound) | 20 parts |
| Water | 44.5 parts |

The above components except the active ingredient are uniformly mixed together to form a solution, and thereto is added the active ingredient. The resulting mixture is throughly stirred, wet-ground by means of sand mill to form a flowable. Upon use, the flowable is diluted up to one fiftieth to one twenty thousandth with water and applied at a rate of 0.005 to 10 kg of the active ingredient per hectare.

The compounds according to the present invention not only exhibit superior insecticidal action on hemiptera insect such as green rice leafhopper (*Nephotettix cincticeps*), lepidoptera insect such as diamounback moth (*Plutella xylostella*), and sanitary insect pests such as pale house mosquito (*Culex pipiens*), but are also useful for expelling mites parasitic on fruits and vegetables such as two-spotted spider mite (*Tetranychus urticae*), Kanzawa spider mite (*Tetranychus kanzawai*), Carmine mite (*Tetranychus cinnabarinus*), citrus red mite (*Panonychus citri*) and European red mite *Panonychus ulmi*), as well as ticks parasitic on animals such as southern cattle tick (*Boophilus microplus*), cattle tick (*Boophilus annulatus*), galf coast tick (*Amblyomma maculatum*), brown-ear tick (*Rhipicephalus appendiculatus*) and (*Haemaphysalis longicornis*). The main features of the compounds of the present invention resides in that the compounds are useful for the prevention or control of blight (or disease) of fruits and vegetables such as powdery mildew, downy mildew, etc. in addition to having the above mentioned insecticidal, acaricidal, nematicidal and fungicidal actions. Accordingly, the compounds of the present invention are an excellent agricultural drug which enables control of pests and blight (or disease) simultaneously. Moreover, they are excellent as an expellent for ticks parasitic on animals such as domestic animals (e.g. cattle, horse, sheep and pig), domestic fowls, and other animals such as dog, cat, rabbit and the like.

The invention is further explained in detail by way of the following test examples.

Test Example 1: Insecticidal test on house fly (*Musca domestica*) adult

One ml of acetone solution containing 1000 ppm of the compound of the invention to be tested was added dropwise to a laboratory dish of 9 cm in diameter so that the solution may be evenly spread over the dish. After completely evaporating the acetone at room temperature, 10 house fly adults were placed in the dish and then the dish was covered with a plastic cap provided with some pores. The dish containing the adults was placed in a thermostatic chamber kept at 25° C. An evaluation was made after 48 hours by counting the adults insects killed and calculating the mortality of the insect in accordance with the following equation:

$$\text{Mortality } (\%) = \frac{\text{number of the insect killed}}{\text{number of the insect placed}} \times 100$$

Incidentally, the test was repeated twice for each compound.

The results thereof are listed in Table 4.

Test Example 2: Insecticidal test on Pale House Mosquito (*Culex pipiens*) larvae 200 ml of 10 ppm aqueous solution of each compound of the invention was placed in a tall dish of 9 cm in diameter and 6 cm in height. Then, 10 of the last instar larvae of Pale House Mosquitos were released in the dish. The tall dish was placed in a thermostatic chamber kept at 25° C., and the number of the mosquitos killed was counted after 96 hours. The mortality was determined as in Test Example 1.

The above test was repeated twice for each compound.

The results are shown in Table 4.

Test Example 3: Contact insecticidal test on Diamondback Moth (*Plutella xylostella*)

A leaf of cabbage was immersed in an aqueous emulsion containing 1000 ppm of each compound of the invention for about 10 seconds, and then air-dried. The leaf thus treated was placed in a dish, into which 10 second instar diamondback moth larvae were released.

The dish was fitted with a cap provided with some pores and then placed in a thermostatic chamber kept at 25° C. The mortality of the diamondback moth after 96 hours was determined in the same manner as in Test Example 1. Incidentally, the test was repeated twice for each compound.

The results thereof are shown in Table 4.

Test Example 4: Contact insecticidal test on 28-spotted Lady Beetle (*Henosepilachna vigintioctopunctata*)

A leaf of tomato was immersed in an aqueous emulsion containing 1000 ppm of each compound of the invention and then air-dried. The leaf thus treated was placed in a laboratory dish, into which 10 second inster 28-spotted lady beetle larvae were released. The dish was then fitted with a cap provided with pores and then placed in a thermostatic chamber kept at 25° C. The number of the larvae killed was checked after 96 hours and the mortality thereof was determined in the same manner as in Test Example 1. Incidentally, the test was repeated twice for each compound.

The test results are shown in Table 4.

Test Example 5: Acaricidal test on Kanzawa Spider Mite (*T. Kanzawa*)

A leaf of kidney bean was cut into a round piece of 1.5 cm in diameter by a leaf punch, and then placed on the moistened filter paper put on a styrol cup of 7 cm in diameter. Each piece of the leaf was inoculated with 10 Kanzawa Spider Mite nymphs. Half a day after the inoculation, each 2 ml of an aqueous emulsion containing 1000 ppm of a compound of the invention diluted with a spreader was applied to each styrol cup by means of a rotary spray tower. The number of the nymph killed was checked after 96 hours and the mortality of the nymph was determined as in Test Example 1. Incidentally, the test was repeated twice for each compound.

The results are shown in Table 4.

Test Example 6: Acaricidal test on Citrus red mite (*Panonychus citri*)

A leaf of Mandarin orange was cut into a round piece of 1.5 cm in diameter by a leaf punch, and then placed on the moistened filter paper put on a styrol cup of 7 cm in diameter. Each piece of the leaf was inoculated with 10 Citrus red mite nymphs. Half a day after the inoculation, each 2 ml of an aqueous emulsion containing 1000 ppm of the active substance with a spreader was applied to each styrol cup by means of a rotary spray tower. The number of the nymph killed was checked after 96 hours and the mortality of the nymph was determined as in Test Example 1.

The results are shown in Table 4.

Test Example 7: Insecticidal test on Green rice leafhopper (*Nephotettix cincticeps*)

Stems and leaves of paddy were immersed into 1000 ppm emulsion of each compound of the invention for 10 seconds, and then the stems and leaves were placed into a glass cylinder. After 10 adults of green rice leafhopper which would show resistance to organic phosphorus type insecticides were released, the glass sylinder was covered with a lid having some pores and placed in a thermostatic chamber kept at 25° C. After 96 hours later, the mortality was determined as in Test Example 1. Incidentally, the test was repeated twice for each compound.

The results are shown in Table 4.

Test Example 8: Nematicidal test on Root-knot Nematode (*Meloidogyne spp.*)

Soil contaminated with root-knot nematode was placed in a styrol cup of 8 cm in diameter. A liquid containing 1000 ppm of an active ingredient was prepared by diluting an emulsifiable concentrate according to the present invention with water and then a spreader was added thereto. The soil contaminated with nematode and placed in the styrol cup was drenched with each 50 ml of the resulting liquid. After 48 hours, a tomato seedling as an indicator was transplanted into the soil thus treated. 30 days after the transplantation, the roots of the tomato were washed with water and the root-knot parasitism was checked by observation and evaluated according to the following rating:

Rating of root-knot parasitism

0 ... no root-knot observed at all.
1 ... a few root-knots observed.
2 ... a medium number of root-knot observed.
3 ... many root-knots observed.
4 ... considerably many root-knots observed.

Incidentally, the test was repeated twice for each compound.

The results are shown in Table 4.

Test Example 9: Test for controlling Downy mildew of cucumber

Employing cucumbers (*Cucumis sativus* L.: variety Sagamihanjiro) which had been grown for about 2 weeks, thereto was sprayed a solution of an emulsifiable concentrate according to the invention which had been adjusted to a predetermined concentration (1000 ppm) at the rate of 20 ml per pot. After each pot was placed overnight in a greenhouse, a suspension of spores of *Pseudoperonospora cubensis* (the concentration of the spores being such that when observed by a 150 magnification microscope, 15 pieces of the spore may be present) was sprayed to the cucumbers for inoculation. The cucumbers to which the spores of *Pseudoperonospora cubensis* had been inoculated were left for 24 hours in a room kept at 25° C. with a relative humidity of 100% and then transported to a greenhouse for observation of disease appearance. Seven days after the inoculation, the percentages of the disease appearance were measured and evaluated according to the following rating:

0 ... no disease appearance
1 ... disease appearance being not more than 5% of the inoculated leaves
2 ... disease appearance being 6-20% of the inoculated leaves
3 ... disease appearance being 21-50% of the inoculated leaves
4 ... disease appearance being 51-90% of the inoculated leaves
5 ... disease appearance being not less than 90% of the inoculated leaves The results are shown in Table 5-I.

Test Example 10: Test for controlling Powdery mildew of cucumber

Employing cucumbers (*Cucumis sativus* L.: variety Sagamihanjiro) which had been grown in pots for about 2 weeks, thereto was sprayed a solution of an emulsifiable concentrate according to the present invention which had been adjusted to a predetermined concentration (1000 ppm) at the rate of 20 ml per pot. After each pot was placed overnight in a greenhouse, a suspension of spores of *Sphaerotheca fuliginea* (the concentration of the spores being such that when observed by a 150 magnification microscope, 25 pieces of the spores may be present) was sprayed to the cucumbers for inoculation. The cucumbers were placed in a greenhouse at 25°–30° C. for observation of disease appearance. Ten days after the inoculation, the percentages of the disease appearance were measured and evaluated according to the same rating as in Test Example 9.

The results are shown in Table 5-II.

Next, the expelling action of the compounds of the invention on ticks parasitic on animals is explained in detail by way of the following test examples.

Test Example 11: Acaricidal test on *Haemaphysalis longicornis*

A 1000 ppm acetone solution of a compound of the invention and an acetone solution as a control were prepared. Inside of a cylindrical glass vessel (2.8 cm in diameter and 10.5 cm in height) was set, to provide a test vessel, a cylindrical filter having an inner surface of 142.9 cm$^2$, side surface of 130.6 cm$^2$ and total surface of bottom and cap surfaces of 24.6 cm$^2$, wherein the filter had previously been immersed in one of the above-mentioned solutions and then dried sufficiently. After 20 tick nymphs were released in this test vessel, the vessel was fitted with a cap provided with the filter and applied with a cotton stopper. After a predetermined time elapsed, the filter was taken out from the vessel, irradiated with light by means of the condenser of a microscope under a binocular stereomicroscope, and observed on migration of the body and movement of the legs of the ticks. Evaluation of life and death of tick was made by regarding such tick as alive that moves its body and legs.

Incidentally, the tick tested is an un-bloodsuck tick nymph which has been incubated from the egg laid by parthenogenetic female tick adult (*Haemaphysalis longicornis*) of Okayama strain which had previously been allowed to such blood from a domestic rabbit.

The results are shown in Table 6.

TABLE 4

| Compound No. | House fly (*Musca domestica*) (1000 ppm) | Pale house mosquito (*Culex pipiens*) (10 ppm) | Diamond-back moth (*Plutella xylostella*) (1000 ppm) | 28-spotted lady beetle (*Henosepilachna vigintioctopunctata*) (1000 ppm) | Kanzawa spider mite (*T. kanzawai*) (1000 ppm) | Citrus red mite (*Panonychus citri*) (1000 ppm) | Green rice leafhopper (*Nephotettix cincticeps*) (1000 ppm) | Root-knot nematode *Meloidogyne* sp. (1000 ppm) |
|---|---|---|---|---|---|---|---|---|
| 1 | 100 | 100 | 100 | 100 | 100 | 100 | 100 | 0 |
| 4 | 100 | 100 | 100 | 100 | 90 | 100 | 100 | 1 |
| 14 | — | 65 | 95 | 100 | 95 | 100 | 100 | 1 |
| 70 | 100 | 100 | 100 | 100 | 100 | 100 | 100 | 0 |
| 72 | 100 | 100 | 100 | 100 | 100 | 100 | 100 | 0 |
| 73 | — | — | — | 100 | 100 | 100 | — | 0 |
| 75 | 100 | 100 | — | 100 | 100 | 100 | 100 | 0 |
| 78 | 70 | 90 | 80 | 100 | 100 | 100 | 100 | 0 |
| 79 | 75 | 95 | 85 | 100 | 100 | 100 | 100 | 0 |
| 80 | 100 | 100 | 100 | 100 | 100 | 100 | 100 | 0 |
| 81 | 100 | 100 | 100 | 100 | 100 | 100 | 100 | 0 |
| 84 | 100 | 100 | 100 | 75 | 100 | 100 | 100 | 1 |
| 87 | 100 | 100 | 100 | 100 | 100 | 100 | 100 | 1 |
| 88 | 100 | 100 | 100 | 100 | 100 | 100 | 100 | 0 |
| 95 | 100 | 100 | 100 | 100 | 100 | 100 | 100 | 0 |
| 97 | 80 | 90 | 100 | 100 | 95 | 100 | 100 | 0 |
| 101 | 100 | 100 | 100 | 100 | 70 | 100 | 100 | 0 |
| 102 | 100 | 100 | 100 | 100 | 100 | 100 | 100 | 0 |
| 103 | 100 | 100 | 100 | 100 | 100 | 100 | 100 | 0 |
| 104 | 100 | 100 | 100 | 100 | 100 | 100 | 100 | 0 |
| 106 | 100 | 100 | 100 | 100 | 100 | 100 | 100 | 0 |
| 107 | 100 | 100 | 100 | 100 | 85 | 100 | 100 | 0 |
| 108 | 100 | 100 | 100 | 100 | 100 | 100 | 100 | 0 |
| 109 | 100 | 100 | 100 | 100 | 100 | 100 | 100 | 0 |
| 110 | — | — | 70 | 90 | 100 | 100 | 100 | 0 |
| 115 | 100 | 100 | 85 | 70 | 90 | 100 | 100 | 1 |
| 126 | — | 100 | — | 100 | 100 | 100 | 100 | 1 |
| 127 | — | 100 | — | 100 | 100 | 100 | 100 | 1 |
| 128 | — | 100 | — | 100 | 100 | 100 | 100 | 0 |
| 129 | 100 | 100 | 100 | 100 | 100 | 100 | 100 | 0 |
| 130 | 100 | 100 | 100 | 100 | 100 | 100 | 100 | 0 |
| 131 | 100 | 100 | — | 100 | 100 | 100 | 100 | 0 |
| 132 | 100 | 100 | 100 | 100 | 100 | 100 | 100 | 0 |
| 133 | 100 | 100 | — | 100 | 100 | 100 | 100 | 0 |
| 134 | 100 | 100 | 100 | 100 | 100 | 100 | 100 | 0 |
| 135 | 100 | 100 | 100 | 100 | 100 | 100 | 100 | 0 |
| 136 | 100 | 100 | — | 100 | 100 | 100 | 100 | 0 |
| 137 | 100 | 100 | 100 | 100 | 100 | 100 | 100 | 0 |
| 138 | 100 | 100 | 100 | 100 | 100 | 100 | 100 | 0 |
| 139 | — | — | — | 100 | 100 | 100 | 100 | 0 |
| 141 | 100 | 100 | — | 100 | 100 | 100 | 100 | 0 |
| 142 | 100 | 100 | — | 100 | 100 | 100 | 100 | 0 |
| 143 | — | 100 | — | 100 | 100 | 100 | 100 | 0 |
| 146 | 100 | 100 | — | 100 | 100 | 100 | 100 | 0 |
| 147 | — | 100 | — | 100 | 100 | 100 | 100 | 0 |
| 148 | 100 | 100 | — | 100 | 100 | 100 | 100 | 0 |
| 149 | 100 | 100 | 100 | 100 | 100 | 100 | 100 | 0 |
| 150 | 100 | 100 | — | — | 100 | 100 | 100 | 1 |
| 151 | 100 | 100 | 100 | 100 | 100 | 100 | 100 | 0 |
| 152 | — | 100 | — | 100 | — | 100 | 100 | 0 |

TABLE 4-continued

| Compound No. | House fly (Musca domestica) (1000 ppm) | Pale house mosquito (Culex pipiens) (10 ppm) | Diamond-back moth (Plutella xylostella) (1000 ppm) | 28-spotted lady beetle (Henosepilachna vigintioctopunctata) (1000 ppm) | Kanzawa spider mite (T. kanzawai) (1000 ppm) | Citrus red mite (Panonychus citri) (1000 ppm) | Green rice leaf-hopper (Nephotettix cincticeps) (1000 ppm) | Root-knot nematode Meloidogyne sp.) (1000 ppm) |
|---|---|---|---|---|---|---|---|---|
| 153 | 100 | 100 | 100 | 100 | 100 | 100 | 100 | 0 |
| 154 | 100 | 100 | 100 | 100 | 100 | 100 | 100 | 0 |
| 155 | 100 | 100 | 100 | 100 | 100 | 100 | 100 | 0 |
| 156 | 100 | 100 | 100 | 100 | 100 | 100 | 100 | 0 |
| 157 | 100 | 100 | 100 | 100 | 100 | 100 | 100 | 0 |
| 158 | 100 | 100 | — | 100 | 100 | 100 | 100 | 0 |
| 159 | 100 | — | — | 100 | 100 | 100 | 100 | 0 |
| 160 | 100 | 100 | — | 100 | 100 | 100 | 100 | 0 |
| 161 | 100 | — | — | 100 | 100 | 100 | 100 | 0 |
| 162 | 100 | 100 | — | — | — | — | 100 | 0 |
| 163 | 100 | 100 | 100 | 100 | 100 | 100 | 100 | 0 |
| 164 | 100 | 100 | — | 100 | 100 | 100 | — | 0 |
| 165 | 100 | 100 | — | 100 | 100 | 100 | 100 | 0 |
| 166 | — | — | 100 | 100 | 100 | 100 | 100 | 0 |
| 167 | — | — | 100 | 100 | 100 | 100 | 100 | 0 |
| 168 | 100 | 100 | 100 | 100 | 100 | 100 | 100 | 0 |
| 169 | 100 | 100 | 100 | 100 | 100 | 100 | 100 | 0 |
| 170 | 100 | 100 | 100 | 100 | 100 | 100 | 100 | 0 |
| 171 | 100 | 100 | — | 100 | 100 | 100 | 100 | 0 |
| 172 | 100 | 100 | — | 100 | 100 | 100 | 100 | 0 |
| 174 | — | — | — | 100 | 100 | 100 | 100 | 0 |
| 176 | — | 100 | 100 | 100 | 100 | 100 | 100 | 0 |
| 177 | — | 100 | 100 | 100 | 100 | 100 | 100 | 0 |
| 178 | 100 | 100 | — | 100 | — | 100 | 100 | — |
| 180 | 100 | 100 | 100 | 100 | 100 | 100 | 100 | 0 |
| 216 | 100 | 100 | 100 | 100 | 70 | 100 | 100 | 1 |
| 224 | 100 | 100 | 95 | 100 | 100 | 100 | 100 | 1 |
| 227 | 100 | 100 | 95 | 100 | 100 | 100 | 100 | 0 |
| 243 | 100 | 100 | 100 | 100 | 100 | 100 | 100 | 0 |
| 244 | 100 | 100 | 100 | 100 | 100 | 100 | 100 | 0 |
| 245 | 100 | 100 | 100 | 100 | 100 | 100 | — | 0 |
| 246 | — | — | — | — | 100 | 100 | 100 | 0 |
| 249 | 100 | 100 | 95 | 100 | 100 | 100 | 100 | 1 |

TABLE 5-I
(Test for controlling Downy mildew of cucumber)

| Compound No. | Degree of disease appearance (1000 ppm) |
|---|---|
| 1 | 0 |
| 4 | 0 |
| 30 | 0 |
| 81 | 0 |
| 95 | 0 |
| 97 | 0 |
| 102 | 0 |
| 70 | 0 |
| 109 | 0 |
| 127 | 0 |
| 131 | 0 |
| 134 | 0 |
| 136 | 0 |
| 138 | 0 |
| 152 | 0 |
| 153 | 0 |
| 176 | 0 |
| 181 | 0 |
| 227 | 0 |
| 243 | 0 |

TABLE 5-II
(Test for controlling Powdery mildew of cucumber)

| Compound No. | Degree of disease appearance (1000 ppm) |
|---|---|
| 1 | 0 |
| 78 | 0 |
| 80 | 0 |
| 81 | 0 |
| 87 | 0 |
| 95 | 0 |
| 70 | 0 |
| 112 | 0 |
| 133 | 0 |
| 138 | 0 |
| 139 | 0 |
| 141 | 0 |
| 149 | 0 |
| 176 | 0 |

TABLE 6
Acaricidal test on *Haemaphysalis longicornis*

| Compound No. | Concentration of solution (ppm) | Ticks killed after treatment (%) 24 hours after treatment | 48 hours after treatment |
|---|---|---|---|
| 70 | 1,000 | 100 | 100 |
| 81 | 1,000 | 100 | 100 |
| 106 | 1,000 | 100 | 100 |
| 109 | 1,000 | 100 | 100 |
| Control (acetone only) | — | 0 | 0 |

What is claimed is:

1. A compound of the formula:

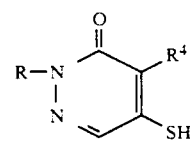

wherein R is a member selected from the group consisting of lower alkyls having from 2 to 4 carbon atoms; and wherein $R^4$ is a member selected from the group consisting of chlorine and bromine.

2. A compound according to claim 1, wherein R is a tert-butyl group and $R^4$ is a chlorine atom.

3. A compound according to claim 1, wherein R is a tert-butyl group and $R^4$ is a bromine atom.

* * * * *